(12) United States Patent
Yamawaki et al.

(10) Patent No.: US 7,488,841 B2
(45) Date of Patent: Feb. 10, 2009

(54) COMPOSITION CONTAINING ACYL GROUP

(75) Inventors: Yukio Yamawaki, Nobeoka (JP); Takao Kitamura, Nobeoka (JP); Yamato Saitou, Nobeoka (JP)

(73) Assignee: Asahi Kasei Chemicals Corporation (JP)

( * ) Notice: Subject to any disclaimer, the term of this patent is extended or adjusted under 35 U.S.C. 154(b) by 565 days.

(21) Appl. No.: 10/525,729

(22) PCT Filed: Aug. 26, 2003

(86) PCT No.: PCT/JP03/10772

§ 371 (c)(1),
(2), (4) Date: Feb. 25, 2005

(87) PCT Pub. No.: WO2004/020394

PCT Pub. Date: Mar. 11, 2004

(65) Prior Publication Data

US 2005/0265951 A1    Dec. 1, 2005

(30) Foreign Application Priority Data

Aug. 27, 2002 (JP) .............................. 2002-247608

(51) Int. Cl.
*C07C 241/00* (2006.01)
*C07C 229/00* (2006.01)

(52) U.S. Cl. ................... 560/169; 560/171; 564/151

(58) Field of Classification Search ................ None
See application file for complete search history.

(56) References Cited

U.S. PATENT DOCUMENTS

| 4,610,983 A | 9/1986 | Takagawa et al. |
| 4,789,758 A | 12/1988 | Takemoto et al. |

FOREIGN PATENT DOCUMENTS

| DE | 2500802 | | 7/1975 |
| FR | 2 257 270 | | 8/1976 |
| JP | 50-2973 | | 1/1975 |
| JP | 50 02973 | | 1/1975 |
| JP | 502973 | * | 1/1975 |
| JP | 55-81655 | | 6/1980 |
| JP | 55-141243 | | 11/1980 |
| JP | 62-263197 | | 11/1987 |
| JP | 10-203956 | | 8/1998 |
| JP | 10-218754 | | 8/1998 |
| JP | 10-219278 | | 8/1998 |
| JP | 2000-44554 | | 2/2000 |
| JP | 2002-167313 | | 6/2002 |
| JP | 2002 167313 A | | 6/2002 |
| WO | WO 83/00146 | | 1/1983 |

OTHER PUBLICATIONS

Nakagaki, et al., "The Basis of Colloid Chemistry", Dainippon Tosho, p. 245, lines 6-11 (Aug. 1, 1976).
Database Crossfire Beilstein Beilstein Institut Zur Foerderung Der Chemischen Wissenschaften Frankfurt AM Main, DE; Database-Accession No. 808847 XP002417126, ACTA Chim. Acad. Sci. Hung., vol. 21, 1959, pp. 71-72.

* cited by examiner

*Primary Examiner*—Karl J Puttlitz
(74) *Attorney, Agent, or Firm*—Finnegan, Henderson, Farabow, Garrett & Dunner, LLP

(57) ABSTRACT

According to the present invention, a process is provided for producing an acyl group-containing composition that includes a step of reacting a long chain N-acyl acidic amino acid anhydride with one or more compounds which have, per molecule, m functional groups of one kind or more selected from the group consisting of hydroxyl, amino and thiol groups in an aqueous solvent and/or a mixed solvent of water and an organic solvent (reaction step). The process makes it possible to produce an acyl group-containing composition that is free from coloration under moderate conditions.

5 Claims, No Drawings

COMPOSITION CONTAINING ACYL GROUP

TECHNICAL FIELD

The present invention relates to an acyl group-containing composition that comprises a long chain N-acyl acidic amino acid derivative and is of high purity and free from much coloration, and to a process for easily producing the same which uses a long chain N-acyl acidic amino acid anhydride.

BACKGROUND ART

There have been known various anionic surfactants useful as components of cleansing agents or cosmetics. It is known that surfactants have to excel in surface activities such as detergency and forming properties. However, with the recent diversification of consumers' needs or an increase in consumers' desire for high-quality articles, they are also required not only to be less irritating to the skin, ophthalmic mucous membrane or the like, but also to make products that are free from coloration or turbidity and give a more favorable feel to the skin. In addition, there is a growing tendency for consumers to require, from the standpoint of burdening the environment, that surfactants have good biodegradability and exert a surface active effect even when used in small amounts.

Traditionally, anionic surfactants such as alkyl sulfates, polyoxyethylene alkyl sulfates and alkyl benzene sulfonates have been used. However, many of these surfactants are not satisfactory in that they strongly irritate the skin at the time of use. Anionic surfactants that are highly safe and excel in biodegradability are amino acid surfactants such as, for example, long chain N-acyl amino-acid salts and derivatives thereof. These surfactants, however, are not satisfactory with respect to surface activity at low concentrations, and the coloration and turbidity of products containing them at low temperatures.

An example of a processes of the prior art for producing a long chain N-acyl acidic amino acid derivative is disclosed in JP-B-50-2973, in which an N-acyl amino acid menthol ester is obtained by dissolving, a long chain N-acyl acidic amino acid anhydride and menthol in toluol or benzol in the presence of p-toluenesulfonic acid as a catalyst at around 100° C. for reaction, and then neutralizing, water-washing and drying the reaction product. In this process, however, coloration in the resultant long chain N-acyl acidic menthol ester (light-yellow) is inevitable because the reaction temperature is high also, industrially implementing the process is difficult because the process involves complicated operations such as neutralization, water washing and drying.

In JP-A-2000-44554, there is disclosed a process for producing a surfactant composed of a long chain N-acyl acidic amino acid derivative, in which a long chain N-acyl acidic amino acid anhydride is reacted with a compound having a hydroxyl group or an amino group, just like the process disclosed in JP-B-50-2973 described above. In this process, in order to prevent coloration in the end product, the reaction is carried out at temperatures higher than the melting point of any one of the ingredients so that the ingredient is in the liquid state during the reaction, or the reaction is carried out in an inert solvent such as toluene while keeping any one of the ingredients in the liquid state. This process is, however, not a satisfactory one with respect to preventing coloration and the reaction yield (purity) of the end product.

For example, in JP-A-2000-44554, an embodiment is described in which N-lauroylglutamic acid anhydride and a sugar, such as sorbitol, or an amino acid, such as L-glutamic acid, are reacted without a solvent at a high temperature of 100° C. or more. In this process, formation of by-products is inevitable and coloration occurs in the product also, the reaction yield is too low to obtain the intended surfactant having high purity. The specification describes that the reaction can be carried out using an inert solvent such as toluene. However, when reacting N-lauroylglutamic acid anhydride and a sugar, such as sorbitol, or an amino acid, such as L-glutamic acid, the reaction has to be carried out at a high temperature of 100° C. or more so that the reaction is that of two phases, a solid phase and a liquid phase, since the solubility of these ingredients in a solvent is low. As a result, the process is not a satisfactory one with respect to the coloration and purity of the end product.

The present inventors have already disclosed in JP-A-2002-167313 an acyl group-containing composition (surfactant) that contains a long chain N-acyl acidic amino acid derivative produced by reacting one or more compounds which have, per molecule, m functional groups of one kind or more selected from the group consisting of hydroxyl, amino and thiol groups with a long chain N-acyl acidic amino acid anhydride, and a process for producing the same. The inventors have made sure that the resultant acyl group-containing composition has surface activity even at low concentrations and does not practically irritate the skin. However, the acyl group-containing composition obtained by this process is not satisfactory in that when it is neutralized and takes the form of an aqueous solution, significant coloration or turbidity occurs and its stability is not good. Further, the reaction yield of the composition is not satisfactorily high, and due to the high impurity content, the resultant composition has to be chromatographed to enhance the end product's purity.

In this reaction process, the reaction is also carried out at temperatures higher than the melting point of any one of the ingredients or by using an inert solvent, just like the process disclosed in JP-A-2000-44554 described above. Accordingly, when reacting a long chain N-acyl acidic amino acid anhydride with an amino acid in an inert solvent such as toluene, since an amino acid is hard to dissolve in solvents other than water, the reaction temperature has to be elevated to allow the reaction to proceed. As a result, by-products are inevitably formed due to the secondary reaction characteristic of the reaction, which causes coloration or turbidity in the end product.

Further, acyl compounds as the reaction products do not highly dissolve in a solvent, either, or have a high melting point. Therefore, in a reaction without a solvent or in an organic solvent, they can sometimes precipitate as intermediate products in the course of the reaction. Due to the necessity to prevent such a situation, the reaction temperature has to be set at around 100° C. or higher.

The present inventors have found that (i) one of the by-products formed in such reactions (reactions carried out at temperatures equal to or higher than the melting point of any one of the ingredients used or by using an inert solvent, just as disclosed in JP-A-2002-167313 and JP-A-2000-44554) has a molecular weight smaller than that of the acyl compound as the intended end product of the reactions by 18 and (ii) the by-product is hard to remove even by separating operations such as separation by chromatography. In fact, such a by-product could not be removed in a separation by chromatography conducted in the examples of the process disclosed in JP-A-2002-167313 and was a cause of coloration in the resultant acyl compound.

Thus, the drawbacks of the prior art lead to a first demand, that is, an acyl group-containing composition, as an anionic surfactant which is less irritating to the skin or the like and has a satisfactory surface activity even at low concentrations, and which contains a long chain N-acyl acidic amino acid derivative, wherein the composition contains a smaller amount of by-products, thereby being free from coloration and turbidity when it takes the form of an aqueous solution, and can be more easily produced in a high yield.

In the meantime, there are various kinds of gelatinous compositions, which are prepared by mixing an oil ingredient with an aqueous solvent and allowing the mixture to take the form of a gel. The term "gel" used herein means a form of compositions which contain liquid over a wide content range, such as a paste, a cream or a jelly, as described in *The Basis of Colloid Chemistry*, Dainippon Tosho, 1976: 245. For example, JP-A-55-141243 discloses an oily gelatinous composition which is prepared by using sodium stearate as a gelling agent and fat and oil as a mediator. The gelatinous composition thus prepared is not satisfactory in that its gel strength is not enough, and cracks are likely to occur in the composition. Moreover, because its hardness is fixed, it does not have arbitrary hardness.

JP-A-55-81655 discloses a gelatinous aromatic substance in which a water-soluble polymer compound, as a gelling agent, is generally added to make the composition gel. However, gelatinous compositions obtained by this process are not satisfactory in that when they are left at temperatures of around 40 to 50° C., their oil ingredients tend to separate or the polymerization degree of the polymers added tends to change which increases or decreases the viscosity of the compositions, and thus their stability deteriorates with time.

Examples of cosmetics which use gelatinous compositions include gelatinous cleansing agents. Such gelatinous cleansing agents are prepared, for example, by mixing an oil ingredient with an aqueous solvent and allowing the mixture to take the form of a gel. Then a water-soluble polymer compound known as a gelling agent is commonly added. When using a gelatinous composition formed with a water-soluble polymer compound for cleansing cosmetics, the resultant cleansing cosmetics are not satisfactory in that they do not spread well, their detergency is questionable and they are sticky even after washing with water. Moreover, their stability deteriorates with time as described above.

Meanwhile, there exists an oil gel which is obtained by making oil to gel with a gelling agent. However, the use of an oil gel makes it hard to adjust the viscosity of gelatinous compositions produced from it. Moreover, when using it for a cleansing agent such as a makeup remover, it cannot be washed from the skin with water, and it needs to be wiped off with tissue paper or the like after use and then cleaned off again with a facial cleanser, etc. There also exist gelatinous compositions which are water-in-oil emulsions. Also in this case, the oil phase is a continuous phase, and thus when using the compositions for cleansing agents, they need to be cleaned off the skin again with a facial cleanser, etc., just like the case of an oil gel. In either case, the hands become sticky with the oil ingredients, and the cleansing agent does not have a favorable feel.

Gelatinous compositions which are oil-in-water emulsions are also known. These types of compositions can be washed from the skin with water without a wipe-off operation as described above. However, their oil ingredients often remain on the skin and cannot be washed off completely from the skin using only water. Further, they have a poor compatibility with oily pollutants and their cleansing performance is not satisfactory. Thus, many compositions of this type have been examined while changing the kind or amount of the oil ingredient or surfactant used. However, there no compositions have been provided that are satisfactory in terms of stability and pleasant feel on the skin.

JP-A-10-219278 discloses compositions of anionic surfactants containing two long-chain acyl groups and two polar groups. The specification states that the compositions can take the form of a gel or a paste if desired; however, it discloses only aqueous solutions of the compositions as cleansing agents and does not describe the gelatinous oil compositions at all.

Thus, the above described drawbacks of the prior art led to a second demand, that is, a gelatinous composition which contains oil ingredients in a stable manner and can have arbitrary hardness in a range of the hardness of a paste to that of a solid, thereby overcoming the above described drawbacks.

Traditionally, cosmetics such as creams, milks and lotions have been allowed to contain a relatively large amount of moisturizing agents such as various types of oil ingredients or glycerol so as to leave the skin feeling moist or give the skin a sufficient moisturizing effect after their application. However, trying to leave the skin feeling further moist or giving the skin a better moisturizing effect often results in leaving the skin feeling excessively oily or sticky or makes the emulsified system unstable, which causes its separation with time, and hence the product deterioration. On the contrary, increasing the content of a surfactant so as to improve the stability of the emulsified system often results in increasing the irritation to the skin. Thus, it has been difficult to satisfy, at the same time, the moist feeling on the skin or the skin moisturizing effect of the composition, the better feeling on the skin after the application of the composition, and the stability of the products of the composition.

JP-A-10-203956 discloses cosmetics which contain a polyhydric alcohol and an amide compound having a specified structure, that excel in skin moisturizing effects, and will not feel sticky on the skin. However, the stability of its emulsified state is not fully satisfied.

JP-A-10-218754 discloses cosmetics composed of an anionic surfactant containing two long-chain acyl groups and two polar groups, powder and/or fine powder, and water. However, the cosmetics are not satisfactory with respect to stability, etc., though they feel better at the time of their application and have an improved skin moisturizing effect.

Thus, the above described drawbacks of the prior art led to a third demand, that is, cosmetics which excel not only in having a moist feeling on the a skin and a skin moisturizing effect, but also in being stable in an emulsified state.

There has been a tendency in recent years to use pigments, instead of dyes, as colorants for aqueous compositions for use in writing implements, recording instruments, printers or liquid cosmetics. This is because pigment colorants are superior in water resistance and light resistance. However, unlike dyes, pigments are insoluble or hardly soluble in water, and therefore it is necessary to disperse pigments stably in water. As dispersants used for this purpose, various types of nonionic or anionic surfactants, cellulose derivatives, or water-soluble polymers such as nonionic polymers have been used independently or in the form of a mixture. However, the method described above cannot disperse pigments well and is insufficient to cope with the occurrence of sedimentation or aggregation with time.

In oil makeup cosmetics, etc., it is generally necessary to disperse an inorganic pigment such as talc, mica, titanium dioxide or kaolin in an oil base material. However, such inorganic pigments are highly hydrophilic, and thus they do not disperse well in an oil base material, which causes problems such as deterioration of product quality.

For example, titanium dioxide is used in cosmetics to screen the skin from ultraviolet rays. The screening effect is produced when the particles of titanium dioxide are in a finely dispersed state. Accordingly, if the particles are not dispersed well and aggregate, the effect becomes insufficient. In delivery apparatuses for writing implements, recording instruments, printers or liquid cosmetics, sedimentation of pigments may cause problems such as clogging of the delivery portions.

Generally, the affinity of dispersants varies depending on whether the pigment is hydrophilic or hydrophobic, and therefore the effectiveness of the dispersion also varies. As a result, there has been no dispersant composition which has satisfactory dispersion stability to hydrophilic pigment and/or hydrophobic pigment.

Thus, the above described drawbacks of the prior art led to a fourth demand, that is, a dispersant composition which has a high dispersion stability with respect to hydrophilic powder and/or hydrophobic powder.

DISCLOSURE OF THE INVENTION

As is apparent from the above description of "Background Art," an object of this invention is to provide an acyl group-containing composition, as an anionic surfactant that is less irritating to the skin or the like and has a sufficient surface activity even at low concentrations, which contains a long chain N-acyl acidic amino acid derivative and forms a smaller amount of by-products, and therefore, does not cause coloration or turbidity when it takes the form of an aqueous solution, and to a process for easily producing the above described composition in a high yield.

Another object of this invention is to provide a gelatinous composition that contains oil ingredients in a stable manner and can have arbitrary hardness in the range of the hardness of a paste to that of a solid.

Another object of this invention is to provide cosmetics which excel not only in having a moist feeling on the skin and a skin moisturizing effect, but also in being stable in an emulsified state.

Still another object of this invention is to provide a dispersant composition which has a high dispersion stability with respect to hydrophilic powder and/or hydrophobic powder.

After directing tremendous research efforts toward the above described problems, the present inventors have ascertained that in the acyl group-containing compositions produced by conventional processes, there exists a reaction by-product, which is a characteristic of the compositions, besides the acyl compound as the intended end product. Thus they have found that (a) such a by-product is formed when a condensation reaction is carried out between a long chain N-acyl acidic amino acid anhydride and one or more compounds which have a hydroxyl, thiol or amino group without a solvent or with a non-aqueous solvent, as described in the documents of the prior art; (b) the tendency toward the by-product formation grows with an increase in the reaction temperature; and (c) the larger the amount of the by-product contained in the acyl group-containing composition, the higher the degree of coloration or turbidity caused in the composition when in the form of an aqueous solution. Mass spectrometry of the by-product has shown that the molecular weight of the by-product is smaller than that of the acyl compound, as the intended product, by 18. This leads to the presumption that the by-product is the acyl compound after it has undergone dehydration (one molecule of $H_2O$). Thus the by-product is defined herein as a "dehydrated acyl compound."

The inventors tried to remove the dehydrated acyl compound from the acyl group-containing composition. Their attempt using, for example, chromatographic treatment increased the purity of the acyl compound to a considerable extent, but could not remove the dehydrated acyl compound. In other words, the method using chromatographic treatment can remove by-products other than the dehydrated acyl compound, but can hardly remove the dehydrated acyl compound. The reason that the dehydrated acyl compound is hard to separate by chromatographic treatment is probably because the polarity of the acyl compound and that of the dehydrated acyl compound are very close to each other.

So then, the inventors examined whether the formation of the dehydrated acyl compound itself can be retarded or not. Surprisingly, the examination revealed that in the process for producing the acyl group-containing composition of this invention in which a long chain N-acyl acidic amino acid anhydride is reacted with a compound having m functional groups of one kind or more selected from the group consisting of hydroxyl, amino and thiol groups, when the reaction was carried out in a water-based solvent (aqueous solvent and/or mixed solvent of water and an organic solvent), which is usually active to anhydrides, the formation of the above described dehydrated acyl compound could be significantly retarded. In other words, the reaction solution obtained through the above described reaction was already colorless and clear before carrying out a by-product removing operation.

Also surprisingly, the inventors have found that in the reaction process in a water-based medium, though the reaction uses an anhydride, an acyl group-containing composition as an object substance can be produced at low temperatures very effectively and in a very high yield, compared with conventional reactions carried out in an inert solvent. Employing a reaction process in which the reaction is carried out in an aqueous medium enables the production of an acyl group-containing composition free from coloration and of high purity without conducting a chromatographic treatment after the reaction. Under conventional reaction conditions, in which no solvent or a non-aqueous solvent is used, the purity of the acyl group-containing composition in the reaction product is no more than about 60% by weight. On the other hand, under reaction conditions in which an aqueous medium is used, an acyl group-containing composition with purity of 90% by weight or more can be easily obtained (this depends on other factors, though). The production process of this invention has overcome the problems of the prior art just by using a water-based solvent as a reaction solvent and has further advanced the purity of the product in a very easy and simple way. This is a remarkable technological improvement in terms of industrial implementation.

Further, unexpectedly, the inventors have also found the following effects. In the production process of this invention, since the reaction is carried out in a water-based solvent, N-acyl acidic amino acid anhydride inevitably undergoes hydrolysis, and a very small amount of a long chain N-acyl acidic amino acid or a salt thereof remains in the acyl group-containing composition. The very small amount of the long chain N-acyl acidic amino acid or the salt thereof remaining in the acyl group-containing composition lowers the Krafft point of the acyl group-containing composition and improves the stability, forming properties, lather creaminess, texture, feelings such as the feeling at the time of washing and a refreshing feeling, and the thickening performance of a cleanser comprising an aqueous solution of the composition.

The present inventors also directed their research efforts toward specifying the characteristics of the acyl group-containing composition of this invention and have found several advantages thereof. They have ascertained, as one of the advantages, that the use of the acyl group-containing composition of this invention makes it possible to provide a gelatinous composition that contains oil ingredients in a stable manner and in a gelatinous state without a gelling agent, excels in stability with time, and can have arbitrary hardness in the range of the hardness of a paste to that of a solid. Surprisingly, the gelatinous composition obtained as above extremely excels in its dispersibility in water. Thus, the inventors have found that the gelatinous composition is a useful composition as a base material for cleansing agents, etc. which can be easily washed with water after application to the skin, do not remain on the skin after application and have an excellent afterfeel and that the gelatinous composition having a viscosity in a certain range has excellent spreading characteristics when applied on the skin or the like. They have also found that the appearance of the gelatinous composition is so transparent that the difference in the index of refraction between the water phase that is composed of a surfactant, a polyhydroxyl compound and water and the oil phase composed of oil ingredients is small.

They have ascertained, as a second advantage of the characteristics of the acyl group-containing composition of this invention, that cosmetics containing a specified amount of the acyl group-containing composition excel not only in providing a moist feeling on the skin and a skin moisturizing effect, but also in their stability in an emulsified state. They have also found that a very stable milky lotion can be produced by using an oil gelatinous composition composed of one kind or more acyl group-containing compositions of this invention, one or more polyhydroxyl compounds having 2 or more hydroxyl groups per molecule and one or more oil ingredients.

Further, the inventors have found a third advantage of the characteristics of the acyl group-containing composition of this invention, that is, the acyl group-containing composition has a high dispersion stability with respect to hydrophilic powder and/or hydrophobic powder.

Specifically, the present invention is made up as follows.

[1] A method of producing an acyl group-containing composition comprising a step of reacting a long chain N-acyl acidic amino acid anhydride represented by the following formula (1):

[Formula 1]

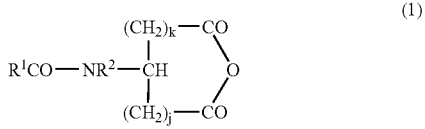

wherein $R^1CO$ represents a long chain acyl group derived from a saturated or unsaturated fatty acid with 2 to 20 carbon atoms; $R^2$ is hydrogen or a lower alkyl group with 1 to 3 carbon atoms which is optionally substituted with a hydroxyl or carboxyl group; j, k are independently any of 0, 1 and 2 and are not 0 at the same time, with one or more compounds having, per molecule, m functional groups of one kind or more selected from the group consisting of hydroxyl, amino and thiol groups in an aqueous solvent and/or a mixed solvent of water and an organic solvent, which is defined as reaction step, wherein the acyl group-containing composition comprises at least one acyl compound represented by the following general formula (2):

[Formula 2]

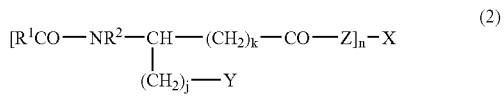

wherein $R^1CO$, $R^2$, and j, k each represent the same as those defined in the above formula (1); n (n is an integer of 2 to 20, including 2 and 20) Zs are bonding portions to which m ($m \geq n$) functional groups of one kind or more selected from the group consisting of hydroxyl, amino and thiol groups substituted on X bind and which are selected independently from the group consisting of —O—, —$NR^3$— ($R^3$ is hydrogen, or an alkyl, an alkenyl, an aryl or an alkylaryl group with 1 to 10 carbon atoms) and —S—; X is a spacer of a straight, branched or cyclic hydrocarbon chain of molecular weight of 1,000,000 or less which optionally has substituents other than hydroxyl, amino and thiol groups and contains or does not contain an aromatic hydrocarbon; n substituents represented by the following general formula (3):

[Formula 3]

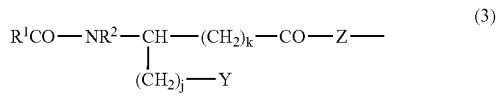

wherein reference characters each represent the same as those defined in the above formula (2), which are attached to X via Z are independent of each other; and Y represents a carboxyl group or the salt thereof.

[2] The method according to the above description [1], wherein in the general formula (2), X is a spacer of a straight, branched or cyclic hydrocarbon chain with 1 to 40 carbon atoms which optionally has substituents other than hydroxyl, amino and thiol groups and contains or does not contain an aromatic hydrocarbon.

[3] The method according to the above description [1] or [2], wherein in said reaction step, the molar ratio of the total of the functional groups contained in the one or more compounds having, per molecule, m functional groups of one kind or more selected from the group consisting of hydroxyl, amino and thiol groups to the long chain N-acyl acidic amino acid anhydride represented by the formula (1) is 0.5 to 1.4 and the pH of the reaction solution is kept at 4 to 14 at the time of reaction.

[4] The method according to any one of the above descriptions [1] to [3], further comprising, as step(s) carried out after said reaction step, either one or both of (i) a step of separating the reaction solution derived from said reaction step into two layers, an organic layer and a water layer, by adjusting the pH of the reaction solution to 1 to 6 using a mineral acid to obtain an organic layer which contains the acyl group-containing composition, which is defined as an acid-precipitation and layer-separation step and (ii) a step of separating, at 35° C. to 80° C., the mixture of the acyl group-containing composition, which contains water-soluble impurities such as inorganic salts, and the medium, which substantially contains water and tertiary butanol as main ingredients, into a water layer and an organic layer containing the acyl group-containing composition to remove impurities in the acyl group-containing composition, which is defined as a washing step.

[5] The method according to any one of the above descriptions [1] to [4], wherein after said reaction step, or after said acid-precipitation and layer-separation step or washing step, the organic solvent is distilled off from the organic layer, which contains the acyl group-containing composition, using a spray evaporator in which a mixed solution is allowed to take the form of a vapor-liquid mixed phase and is sprayed within the evaporator to evaporate the solvent.

[6] An acyl group-containing composition comprising at least one acyl compound represented by the following formula (2):

[Formula 2]

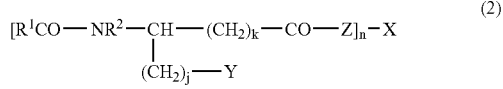

wherein $R^1CO$ represents a long chain acyl group derived from a saturated or unsaturated fatty acid with 2 to 20 carbon atoms; $R^2$ is hydrogen or a lower alkyl group with 1 to 3 carbon atoms which is optionally substituted with a hydroxyl or carboxyl group; j, k are independently any of 0, 1 and 2 and are not 0 at the same time; n (n is an integer of 2 to 20, including 2 and 20) Zs are bonding portions to which m (m≧n) functional groups of one kind or more selected from the group consisting of hydroxyl, amino and thiol groups substituted on X bind and which are selected independently from the group consisting of —O—, —NR³— (R³ is hydrogen, or an alkyl, an alkenyl, an aryl or an alkylaryl group with 1 to 10 carbon atoms) and —S—; X is a spacer of a straight, branched or cyclic hydrocarbon chain of molecular weight of 1,000,000 or less which optionally has substituents other than hydroxyl, amino and thiol groups and contains or does not contain an aromatic hydrocarbon; n substituents represented by the following general formula (3):

[Formula 3]

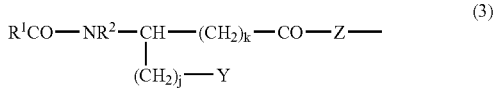

wherein reference characters each represent the same as those defined in the above formula (2), which are attached to X via Z are independent of each other; and Y represents a carboxyl group or the salt thereof, wherein the content of the acyl compound in the composition is 70% by weight or more, the content of free fatty acid is 3% by weight or less, and the content of a compound whose molecular weight is smaller than that of the acyl compound by 18 is 5% or less in terms of its area ratio to the acyl compound which is obtained by the analysis of liquid chromatography using a detector at 205 nm.

[7] The composition according to the above description [6], comprising 0.5 to 30% by weight of a long chain N-acyl acidic amino acid or a salt thereof.

[8] The composition according to the above description [6] or [7], wherein in the general formula (2), X is a spacer of a straight, branched or cyclic hydrocarbon chain with 1 to 40 carbon atoms which optionally has substituents other than hydroxyl, amino and thiol groups and contains or does not contain an aromatic hydrocarbon.

[9] The composition according to any one of the above descriptions [6] to [8], wherein in the general formula (2), $R^1CO$ is a long chain acyl group derived from a saturated or unsaturated fatty acid with 8 to 20 carbon atoms.

[10] The composition according to any one of the above descriptions [6] to [9], wherein in the general formula (2), X has at least one group independently selected from the group consisting of carboxyl, sulfonic acid, sulfate ester and phosphate ester groups and the salts thereof.

[11] The composition according to any one of the above descriptions [6] to [10], comprising 0.2 to 1.5 equivalent of basic substance, as a counter ion, per 1 equivalent of dissociated groups in said acyl group-containing compound.

[12] The composition according to any one of the above descriptions [6] to [11], wherein the transmittances at 430 nm and 550 nm are both 90% or more when said acyl group-containing composition is formed into an aqueous solution having a solids content of 20% by weight and a pH of 10.

[13] The composition according to the above description [10] or [11], further comprising other surfactant (s).

[14] The composition according to any one of the above descriptions [6] to [13], comprising at least one acyl compound represented by the general formula (2) which is produced through a step of reacting a long chain N-acyl acidic amino acid anhydride represented by the following formula (1):

[Formula 1]

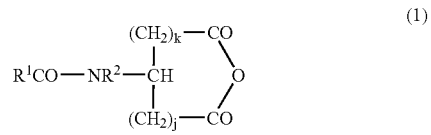

wherein reference characters represent the same as those defined above, with one or more compounds having, per molecule, m functional groups of one kind or more selected from the group consisting of hydroxyl, amino and thiol groups in water and/or a mixed solvent of water and an organic solvent, which is defined as reaction step.

[15] The composition according to the above description [14], wherein the one or more compounds having, per molecule, m functional groups of one kind or more selected from the group consisting of hydroxyl, amino and thiol groups independently have, per molecule, at least one group, other than hydroxyl, amino and thiol groups, selected from the group consisting of carboxyl, sulfonic acid, sulfate ester and phosphate ester groups and the salts thereof.

[16] The composition according to descriptions [14] or [15], wherein the composition is produced by carrying out, after said reaction step, either one or both of (i) a step of separating the reaction solution derived from said reaction step into two layers, an organic layer and a water layer, by adjusting the pH of the reaction solution to 1 to 6 using a mineral acid to obtain an organic layer containing the acyl group-containing composition, which is defined as an acid-precipitation and layer-separation step and (ii) a step of separating, at 35° C. to 80° C., the mixture of the acyl group-containing composition, which contains water-soluble impurities such as inorganic salts, and the medium, which substantially contains water and tertiary butanol as main ingredients, into a water layer and an organic layer containing the acyl group-containing composition to remove impurities in the acyl group-containing composition, which is defined as a washing step.

[17] The composition according to any one of the above descriptions [14] to [16], wherein the composition is produced by distilling off the organic solvent, after said reaction step, or after said acid-precipitation and layer-separation step or washing step, from the organic layer which contains the acyl group-containing composition using a spray evaporator in which a mixed solution is allowed to take the form of a vapor-liquid mixed phase and is sprayed within the evaporator to evaporate the solvent.

[18] A composition in the form of a liquid, a solid, a gel, a paste or a mist, comprising one or more of the acyl group-comprising compositions according to any one of the above descriptions [6] to [17].

[19] A cosmetic composition in the form of a liquid, a solid, a gel, a paste or a mist, comprising one or more of the acyl group-containing compositions according to any one of the above descriptions [6] to [17].

[20] The cosmetic composition according to the above description [19], further comprising one or more polyhydroxyl compounds.

[21] The cosmetic composition according to the above description [20], wherein the content of polyhydroxyl compounds in the above described cosmetic composition is 0.1 to 60% by weight and the weight ratio of the content of the acyl group-containing compositions to the content of the polyhydroxyl compounds in said cosmetic composition is 10/1 to 1/100.

[22] The cosmetic composition according to the above description [20] or [21], further comprising one or more oil ingredients and being in the form of a gel.

[23] A gelatinous composition comprising one kind or more of the acyl group-containing compositions according to any one of the above descriptions [6] to [17], one or more polyhydroxyl compounds and one or more oil ingredients, wherein the water content in the gelatinous composition is 50% by weight or less and the composition of the gelatinous composition is such that 1) the total amount of the acyl group-containing compositions is 0.1 to 40% by weight, 2) the total amount of the polyhydroxyl compounds is 1 to 60% by weight, and 3) the total amount of the oil ingredients is 1 to 95% by weight.

[24] The gelatinous composition according to the above description [23], wherein the difference in refractive index at 20° C. between the water layer containing the acyl group-containing composition(s), the polyhydroxyl compound(s) and water, and the oil layer containing the oil ingredients, in the gelatinous composition is ±0.05 or less.

[25] The gelatinous composition according to the above description [23] or [24], wherein its viscosity at 25° C. is 1,000 to 200,000 mPa·s.

[26] Use of the gelatinous composition according to any one of the above descriptions [23] to [25] for cleansing agents.

[27] A cosmetic composition, prepared by emulsifying the gelatinous composition according to any one of the above descriptions [23] to [25].

[28] A dispersant composition which comprises one or more of the acyl group-containing compositions according to any one of the above descriptions [6] to [17] and is in the form of a liquid, a solid, a gel, a paste or a mist.

BEST MODE FOR CARRYING OUT THE INVENTION

In the following the present invention will be described in detail particularly in terms of its embodiments.

The acyl group-containing composition according to this invention contains an acyl compound having, per molecule, more than one acyl group as a hydrophobic group and more than one hydrophilic group, as represented by the general formula (2).

The acyl groups represented by $R^1CO$ in the general formula (2) are independent of each other. In other words, they may be different or the same. They may be any acyl groups as long as they are derived from a saturated or unsaturated fatty acid with 2 to 20 carbon atoms. It does not matter whether they are straight-chain, branched-chain or cyclic-chain acyl groups.

Examples of $R^1CO$ include acyl groups derived from the following acids: straight-chain fatty acids such as acetic acid, propionic acid, butyric acid, pentanoic acid, hexanoic acid, heptanioc acid, caprylic acid, pelargonic acid, capric acid, undecanoic acid, lauric acid, tridecanoic acid, myristic acid, pentadecanoic acid, palmitic acid, margaric acid, stearic acid, nonadecanoic acid and arachic acid; branched-chain fatty acids such as 2-butyl-5-methylpentanoic acid, 2-isobutyl-5-methylpentanoic acid, dimethyloctanoic acid, dimethylnonanoic acid, 2-butyl-5-methylhexanoic acid, methylundecanoic acid, dimethyldecanoic acid, 2-ethyl-3-methylnonanoic acid, 2,2-dimethyl-4-ethyloctanoic acid, methyldocosanoic acid, 2-propyl-3-methylnonanoic acid, methyltridecanoic acid, dimethyldodecanoic acid, 2-butyl-3-methylnonanoic acid, methyltetradecanoic acid, ethyltridecanoic acid, propyldodecanoic acid, butylundecanoic acid, pentyldecanoic acid, hexylnonanoic acid, 2-(3-methylbutyl)-3-methylnonanoic acid, 2-(2-methylbutyl)-3-methylnonanoic acid, butylethylnonanoic acid, methylpentadecanoic acid, ethyltetradecanoic acid, propyltridecanoic acid, butyldodecanoic acid, pentylundecanoic acid, hexyldecanoic acid, heptylnonanoic acid, dimethyltetradecanoic acid, butylpentylheptanoic acid, trimethyltridecanoic acid, methylhexadecanoic acid, ethylpentadecanoic acid, propyltetradecanoic acid, butyltridecanoic acid, pentyldodecanoic acid, hexylundecanoic acid, heptyldecanoic acid, methylheptylnonanoic acid, dipentylheptanoic acid, methylheptadecanoic acid, ethylhexadecanoic acid, propylpentadecanoic acid, butyltetradecanoic acid, pentyltridecanoic acid, hexyldodecanoic acid, heptylundecanoic acid, octyldecanoic acid, dimethylhexadecanoic acid, methyloctylnonanoic acid, methyloctadecanoic acid, ethylheptadecanoic acid, dimethylheptadecanoic acid, methyloctyldecanoic acid, methylnonadecanoic acid, dimethyloctadecanoic acid and butylheptylnonanoic acid; straight-chain monoen acids such as octene acid, nonene acid, decene acid, caprolenic acid, undecylenic acid, linderic acid, obtusilic acid, lauroleinic acid, tridecene acid, tsuzuic acid, myristoleic acid, pentadecene acid, hexadecene acid, palmitoleic acid, heptadecene acid, octadecene acid, oleic acid, nonadecene acid and gondoic acid; branched monoene acids such as methylheptene acid, methylnonene acid, methylundecene acid, dimethyldecene acid, methyldodecene acid, methyltridecene acid, dimethyldodecene acid, dimethyltridecene acid, methyloctadecene acid, dimethylheptadecene acid and ethyloctadecene acid; di- or tri-ene acids such as linoleic acid, linoelaidic acid, eleostearic acid, linolenic acid, linolenelaidic acid, pseudoeleostearic acid, parinaric acid and arachidonic acid; acetylenic acids such as octynoic acid, nonynoic acid, decynoic acid, undecynoic acid, dodecynoic acid, tridecynoic acid, tetradecynoic acid, pentadecynoic acid, heptadecynoic acid octadecynoic acid, nonadecynoic acid and dimethyloctadecynoic acid; and cyclic acids such as methyleneoctadecenoic acid, methyleneoctdecanoic acid, aleprolic acid, aleprestic acid, aleprylic acid, alepric acid, hydonocarpic acid, chaulmoogric acid, gorlic acid, α-cyclopentyl acid, α-cyclohexyl acid and α-cyclopentylethyl acid.

$R^1CO$ may be acyl groups derived from fatty acids obtained from natural fats and oils, as long as they are derived from mixed fatty acids which contain 80% or more of the above described saturated or unsaturated fatty acids with 2 to 20 carbon atoms. Examples of such acyl groups include acyl groups derived from, for example, coconut oil fatty acid, palm oil fatty acid, linseed oil fatty acid, sunflower oil fatty acid, soybean oil fatty acid, sesame oil fatty acid, castor oil fatty acid, olive oil fatty acid, camellia oil fatty acid, rapeseed oil fatty acid and palm stone oil fatty acid.

The kind of the $R^1CO$ can be selected depending on the purpose for which they are used, since surface activity varies depending on the kind of the $R^1CO$. When using the composition as a surfactant, preferably $R^1CO$ with 8 to 20 carbon atoms are selected.

In the general formula (2), $R^2$ represents a hydrogen atom or a lower alkyl group with 1 to 3 carbon atoms which is optionally substituted with a hydroxyl, carboxyl, sulfonic acid, sulfate ester or phosphate ester group, or a salt thereof. Examples of such lower alkyl groups include methyl, ethyl, propyl, isopropyl, hydroxymethyl, hydroxyethyl, hydroxyl(iso)propyl, dihydroxy(iso)propyl, carboxymethyl, carboxyethyl, carbpxypropyl and sulfoethyl groups.

In the general formula (2), n substituents (formula (3)) attached to X are independent of each other. In other words, they may be different or the same. The formula (3) represents, what is called, N-acylated acidic amino acid, and it does not matter which optically isomeric configuration each substituent has. It may be a D-isomer, L-isomer or racemate.

The acidic amino acid is a monoaminodicarboxylic acid having 2 carboxyl groups and one amino group per molecule. The amino group may be a N-methyl group or a N-ethyl group. It does not matter which optically isomeric configuration the acidic amino acid has. It may be a D-isomer, L-isomer or racemate. Examples of an acidic amino acid include glutamic acid, asparagic acid, lanthionine, β-methyllanthionine, cystathionine, dienecholic acid, felinine, aminomalonic acid, β-oxyasparagic acid, α-amino-α-methylsuccinic acid, β-oxygulutamic acid, γ-oxygulutamic acid, γ-methylgulutamic acid, γ-methylenegulutamic acid, γ-methyl-γ-oxygulutamic acid, α-aminoadipic acid, α-amino-γ-oxyadipic acid, α-aminopimelic acid, α-amino-γ-oxypimelic acid, β-aminopimelic acid, α-aminosuberic acid, α-aminosebacic acid and pantothenic acid.

Preferably, n substituents (general formula (3)) attached to X are N-acylated L-acidic amino acid molecules, because such substituents allow the acyl group-containing composition of this invention to excel in biodegradability.

In the general formula (2), n Zs attached to X are bonding portions (—O—, —$NR^3$— and —S—) resulting from m (m≧n) functional groups (hydroxyl, amino or thiol groups) substituted on X bind. They are independent of each other. In other words, they may be different or the same. $R^3$ is hydrogen, or an alkyl, an alkenyl, an aryl or an alkylaryl group with 1 to 10 carbon atoms. Preferably, n Zs attached to X are bonding portions (—$NR^3$—) resulting from amino groups substituted on X.

In the general formula (2), X is a spacer of a straight, a branched or a cyclic hydrocarbon chain having a molecular weight of 1,000,000 or less which has m functional groups of one kind or more selected from the group consisting of hydroxyl, amino and thiol groups and contains or does not contain an aromatic hydrocarbon. X may have substituents other than said hydroxyl, amino and thiol groups.

In the general formula (2), preferably X is an m-valent compound residue which has a molecular weight of 1,000,000 or less and has m functional groups of one kind or more selected from the group consisting of hydroxyl, amino and thiol groups and X is compound residue which may have substituents other than hydroxyl, amino and thiol groups. The m-valent compound described above means a compound capable of forming linkages resulting from m functional groups. It does not matter which optically isomeric configuration the compound has. It may be a D-isomer, L-isomer or racemate.

Examples of such m-valent compounds include: amino acids such as serine, threonine, cysteine, cystine, cystinedisulfoxide, cystathionine, methionine, arginine, lysine, tyrosine, histidine, tryptophan and oxyproline; compounds having, per molecule, an amino group(s) and a hydroxyl group(s) such as aminoethanol, aminopropanol, aminobutanol, aminopentanol, aminohexanol, aminopropanediol, aminoethylethanolamine, aminoethylaminoethanol, aminocresol, aminonaphthol, aminonaphtholsulfonic acid, aminohydroxybenzoic acid, aminohydroxydibutanioc acid, aminophenol, aminophenethyl alcohol and glucosamine; compounds having, per molecule, a thiol group and a hydroxyl group(s) such as mercaptoethanol, mercaptphenol, mercaptpropanediol and glucothiose; and compounds having, per molecule, a thiol group and an amino group such as aminothiophenol and aminotriazolethiol. The m-valent compounds may be proteins, peptides or the hydrolyzed products thereof.

In the general formula (2), preferably X is an m-valent (m≧n) polyhydroxyl compound residue of molecular weight of 1,000,000 or less which optionally has substituents other than a hydroxyl group. The m-valent polyhydroxyl compound herein means a compound capable of forming m ester linkages. It does not matter which optically isomeric configuration the compound has. It may be a D-isomer, L-isomer or racemate.

Examples of m-valent polyhydroxyl compounds include: divalent hydroxyl compounds such as ethylene glycol, 1,2-propanediol, 1,3-propanediol, 1,2-butanediol, 1,3-butanediol, 1,4-butanediol, pentanediol, 1,6-hexanediol, cyclohexanediol, dimethylolcyclohexane, neopentyl glycol, 1,8-octanediol, 2,2,4-trimethyl-1,3-pentanediol, isoprene glycol, 3-methyl-1,5-pentanediol, sorbite, catechol, resorcin, hydroquinone, bisphenol A, bisphenol F, hydrogenated bisphenol A, hydrogenated bisphenol F, dimerdiol, dimethylolpropionic acid, dimethylolbutanoic acid, tartaric acid, dihydroxytataric acid, mevalonic acid, 3,4-dihydroxycinnamic acid, 3,4-dihydroxyhydrocinnamic acid, hydroxybenzoic acid, dihydroxystearic acid, dihydroxyphenylalanine and the isomers thereof; trivalent polyhydroxyl compounds such as glycerol, trioxyisobutane, 1,2,3-butanetriol, 1,2,3-pentanetriol, 2-methyl-1,2,3-propanetriol, 2-methyl-2,3,4-butanetriol, 2-ethyl-1,2,3-butanetriol, 2,3,4-pentanetriol, 2,3,4-hexanetriol, 4-propyl-3,4,5-heptanetriol, 2,4-dimethyl-2,3,4-petanetriol, 1,2,4-butanetriol, 1,2,4-pentanetriol, trimethylolethane, trimethylolpropane, diethanolamine, triethanolamine, trihydroxystearic acid; tetravalent polyhydroxyl compounds such as pentaerythritol, erythritol, 1,2,3,4-pentanetetrol, 2,3,4,5-hexanetetrol, 1,2,4,5-pentanetetrol, 1,3,4,5-hexanetetrol, diglycerol and sorbitan; pentavalent polyhydroxyl compounds such as adonitol, arabitol, xylitol and triglycerol; hexavalent polyhydroxyl compounds such as dipentaerythritol, sorbitol, mannitol, iditol, inositol, dalsitol, talose and allose; and the dehydration condensation products thereof.

Examples of m-valent polyhydroxyl compounds include saccharides: for example, monosaccharides, such as tetrose such as erythrose, threose and erythrulose, pentose such as ribose, arabinose, xylose, lyxose, xylulose and ribulose, hexose such as allose, altrose, glucose, mannose, gulose, idose, galactose, tarose, fructose, sorbose, psicose and tagatose; and oligosaccharides such as maltose, isomaltose, cellobiose, gentiobiose, meribiose, lactose, turanose, treharose, saccharose, mannitriose, cellotriose, gentianose, raffinose, melezitose, cellotetrose and stachyose.

M-valent polyhydroxyl compounds may be other saccharide residues such as heptose, deoxy-saccharides, amino-saccharides, thio-saccharides, seleno-saccharides, aldonic acid, uronic acid, sugar acid, ketaldonic acid, anhydrosugars, unsaturated sugars, sugar esters, sugar ethers and glycoside, or polysaccharides such as starch, glycogen, cellulose, chitin and chitosan, or hydrolyzed products thereof.

In the general formula (2), preferably X is an m-valent polyamino compound residue of molecular weight of 1,000,000 or less which optionally has substituents other than an amino group. The m-valent polyamino compound herein means a compound capable of forming m acid amido linkages. It does not matter which optically isomeric configuration the compound has. It may be a D-isomer, L-isomer or racemate.

Examples of m-valent polyamino compounds include: aliphatic diamines such as N,N'-dimethylhydrazine, ethylenediamine, N,N'-dimethylethylenediamine, diaminopropane, diaminobutane, diaminopentane, diaminohexane, diaminoheptane, diaminooctane, diaminononane, diaminodecane, diaminododecane, diaminoadipic acid, diaminopropanoic acid, diaminobutanoic acid and the isomers thereof; aliphatic triamines such as diethylenetriamine, triaminohexane, triaminododecane, 1,8-diamino-4-aminomethyl-octane, 2,6-diaminocapric acid-2-aminoethyl ester, 1,3,6-triaminohexane, 1,6,11-triaminoundecane, di(aminoethyl)amine and the isomers thereof; alicyclic polyamines such as diaminocyclobutane, diaminocyclohexane, 3-aminomethyl-3,5,5-trimethylcyclohexylamine and triaminocyclohexane; aromatic polyamines such as diaminobenzene, diaminotoluene, diaminobenzoic acid, diaminoanthraquinone, diaminobenzenesulfonic acid, and the isomers thereof; aliphatic-aromatic polyamines such as diaminoxylene, di(aminomethyl)benzene, di(aminomethyl)pyridine, di(aminomethyl)naphthalene and the isomers thereof; and hydroxyl group-substituted polyamines such as diaminohydroxypropane and the isomers thereof.

In the general formula (2), preferably X is an m-valent polythiol compound residue of molecular weight of 1,000,000 or less which optionally has substituents other than a thiol group. The m-valent polythiol compound herein means a compound capable of forming m thioester linkages. It does not matter which optically isomeric configuration the compound has. It may be a D-isomer, L-isomer or racemate.

Examples of m-valent polythiol compounds include dithiol compounds such as dithioethylene glycol, dithioerythritol and dithiothreitol.

Of the above described compound residues, residues with 1 to 40 carbon atoms are preferable as X and those with 1 to 20 carbon atoms are more preferable.

Preferably X contains, as substituents, at least one carboxyl group, sulfonic acid group, sulfate ester group, phosphate ester group or the salts thereof independently, because with such X, the acyl group-containing composition of this invention excels in solubility in weak-acid solution. Preferably X is in the naturally occurring form, because with such X, the acyl group-containing composition of this invention excels in biodegradability.

In the general formula (2), the carboxyl group represented by Y and the carboxyl group(s), sulfonic acid group(s), sulfate ester group(s) or phosphate ester group(s) contained in X are capable of forming salts with various basic substances. Examples of such salts include alkaline metal salts, alkaline earth metal salts, ammonium salts, organic amine salts and basic amino acid salts. Concrete examples are salts of one or more basic substances selected from the group consisting of alkaline metals such as sodium, potassium and lithium, alkaline earth metals such as calcium and magnesium, metals such as aluminum and zinc, organic amines such as ammonia, monoethanolamine, diethanolamine, triethanolamine and triisopropanolamine, and basic amino acids such as arginine and lysine. Of these salts, sodium salts, potassium salts, organic amine salts and basic amino acid salts are preferable.

Now, a method for producing an acyl group-containing composition of this invention will be described. The method includes a step of reacting a long chain N-acyl acidic amino acid anhydride and a compound-having, per molecule, m functional groups of one kind or more selected from the group consisting of hydroxyl, amino and thiol groups in water and/or a mixed solvent of water and an organic solvent.

The present inventors have found that the above described reaction step produces the following effects. First, even if amino acids or saccharides, which are compounds slightly soluble in solvents other than water, are used as ingredients, such ingredients, and besides, acyl compounds as products can be dissolved in the reaction solvent under reaction conditions of around room temperature or lower, and therefore the reaction solution can be kept in a uniform state until the reaction is completed. Thus, the reaction is allowed to progress under moderate conditions, which retards the formation of by-products, resulting in the production of an acyl group-containing composition of high purity. Particularly the amount of dehydrated acyl compound, a by-product which conventional processes cannot avoid, can be restricted to a very small amount.

A second effect is as follows. Since the production method of this invention uses a water-based solvent as a reaction solvent, there remains in the acyl group-containing composition a long chain N-acyl acidic amino acid or a salt thereof, which is produced by the inevitable hydrolysis of N-acyl acidic amino acid anhydride during the reaction. The inventors have found that this small amount of a long chain N-acyl acidic amino acid or a salt thereof remaining in the acyl group-containing composition produces unexpected effects. Specifically, the acyl group-containing composition of this invention is free from coloration, and besides, its following properties are improved due to the presence of the long chain N-acyl acidic amino acid or the salt thereof.

Lowers the Krafft point of the acyl group-containing composition, thereby improving its utility at low temperatures.

Increases the solubility of the acyl group-containing composition in water, thereby make possible its use in a wider and lower pH range (particularly in the weak-acid range).

Improves the stability of cleansing agents composed of the aqueous solution of the acyl group-containing composition.

Improves the forming properties of cleansing agents composed of the aqueous solution of the acyl group-containing composition and the creaminess of the lather.

Makes finer the lather texture of cleansing agents composed of the aqueous solution of the acyl group-containing composition.

Improves the touch of cleansing agents composed of the aqueous solution of the acyl group-containing composition at the time of washing.

Improves the feeling of refreshment users are given after cleansing using cleansing agents composed of the aqueous solution of the acyl group-containing composition.

Improves the thickening properties of an aqueous solution of the acyl group-containing composition with a thickening agent.

From the viewpoint of the above described properties, preferably the acyl group-containing composition contains 0.5 to 30% by weight of a long chain N-acyl acidic amino acid or the salt thereof, more preferably 1 to 15% by weight and much more preferably 1 to 10% by weight.

A long chain N-acyl acidic amino acid anhydride represented by the general formula (1) and used in this invention is an acidic amino acid having been acylated by a saturated or unsaturated fatty acid residue with 2 to 20 carbon atoms which may be straight-, branched- or cyclic-chain. The amino group of the amino acid may be either N-methylated one or N-ethylated one. It does not matter which optically isomeric configuration the amino acid has. It may be a D-isomer, L-isomer or racemate.

Examples of such amino acids include a long chain N-acylglutamic acid, asparagic acid, lanthionine, β-methyllanthionine, cyctathionine, diencholic acid, felinine, aminomalonic acid, β-oxyasparagic acid, α-amino-α-methylsuccinic acid, β-oxyglutamic acid, γ-oxyglutamic acid, γ-methylglutamic acid, γ-methyleneglutamic acid, γ-methyl-γ-oxyglutamic acid, α-aminoadipic acid, α-amino-γ-oxyadipic acid, α-aminopimelic acid, α-amino-γ-oxypimelic acid, β-aminopimelic acid, α-aminosuberic acid, α-aminosebacic acid and pantothenic acid. Of these acidic amino acids, L-acidic amino acids are preferable, because when using them, the resultant acyl group-containing composition of this invention excels in biodegradability.

Long chain N-acyl acidic amino acid anhydrides can be obtained easily by commonly used synthetic methods. For example, even crude crystals of a long chain N-acyl acidic amino acid anhydride obtained by reacting a carboxylic acid anhydride such as acetic anhydride with a long chain N-acyl acidic amino acid and then subjecting the reaction solution to crystal precipitation, filtration and drying can be directly applied to this invention.

The reaction step in the production method of this invention can be carried out by, for example, mixing a compound having m functional groups of one kind or more, which are selected from the group consisting of hydroxyl, thiol and amino groups, and a long chain N-acyl acidic amino acid anhydride, while stirring, in an aqueous solvent or a mixed solvent of water and an organic solvent(s) (a single kind of or a mixture of more than one kind of organic solvent). The important point is that the compound having m functional groups of one kind or more selected from the group consisting of hydroxyl, amino and thiol groups is dissolved in the reaction solvent under the reaction conditions.

When reacting an amino acid or saccharide with a long chain N-acyl acidic amino acid anhydride by a conventional process, the ingredients have to be reacted in such a state that they are dispersed in a solution, because there is no appropriate solvent. Accordingly, severe reaction conditions, for example, elevated reaction temperatures have to be employed. On the other hand, in the method of this invention where the reaction medium is a water-based one, reaction can be carried out under very moderate conditions. And the moderate reaction conditions allow the formation of by-products to be restrained to a minimum.

The mixing ratio of water and an organic solvent applicable is in the range of 100/0 to 1/99 (volume ratio) and preferably 100/0 to 20/80 (volume ratio). The state of such a mixed solvent may be a uniform phase or non-uniform phase such as 2-phase as long as no precipitation occurs.

Examples of organic solvent applicable include tetrahydrofuran, benzene, toluene, xylene, carbon tetrachloride, chloroform, acetone, methyl ethyl ketone, cyclohexane, dioxane and tertiary butanol. The organic solvent used in the production method of this invention need not be of high purity, and it may be a water-containing organic solvent produced as, for example, water azeotrope. Organic solvents recovered from a reaction purification system can also be used without purification.

In the reaction step of the production method of this invention, the reaction temperature is not particularly limited; however, generally, lower reaction temperatures are advantageous, because the lower the reaction temperature becomes, the smaller the formation rate of the hydrolyzed product of a long chain N-acyl acidic amino acid anhydride becomes. However, too low a temperature may cause an increase in viscosity of the reaction solution or a setting of the same, which results in an impossibility of mixing or a significant decrease in reaction rate. Thus, a reaction temperature should be selected from a temperature range that permits such situations to be avoided. The reaction temperature may be changed with time. Normally, the reaction temperature is in the range of −5 to 100° C., preferably in the range of 0 to 60° C. and more preferably in the range of 5 to 40° C.

In the reaction step of the production method of this invention, the concentration of each ingredient prepared is not particularly limited. However, the concentration should be such that it allows the operation of mixing under stirring to be carried out during the reaction. Preferably the concentration is 0.1 to 50% by weight in terms of solids concentration.

In the reaction step of the production method of this invention, preferably the reaction is carried out while keeping the pH of the reaction solution in the range of 4 to 14. Alkaline substances used for adjusting the pH of the reaction solution include: for example, inorganic bases such as sodium hydroxide, potassium hydroxide, calcium hydroxide, barium hydroxide; and organic bases such as ammonia and organic ammonium. Preferably, an aqueous solution of an inorganic base is used.

If the pH of the reaction solution is lower than 4, by-products due to the hydrolysis of a long chain N-acyl acidic amino acid anhydride are increased, whereas if the pH is higher than 14, a larger amount of alkaline substance than needed is consumed, and therefore the amount of acid consumed in the next step is also increased, though no substantial disadvantages occur. Thus, from the viewpoint of resource consumption, it is preferable to keep the pH of the reaction solution in the range of 4 to 14, more preferably in the range of 6 to 13 and much more preferably in the range of 9 to 12.

In the reaction step of the production method of this invention, the reaction can be carried out in the following manner. Specifically, it can be carried out in a batchwise operation in which first, all of the prescribed amount of ingredients: one or more compounds selected from the compounds each having a hydroxyl, thiol or amino group; a solvent; and a long chain N-acyl acidic amino acid anhydride are prepared in a stirring vessel, and then an alkaline substance is fed to the mixed solution to keep the pH of the solution in a specified range. Or it can be carried out in a semi-batch operation in which first, one kind or more compounds having m functional groups of one kind or more, which are selected from the group consisting of hydroxyl, thiol and amino groups and a solvent are prepared, and then a long chain N-acyl acidic amino acid anhydride are continuously fed to form the mixed solution while feeding an alkaline substance to keep the pH of the solution in a prescribed range. Or it can be carried out in a continuous feeding operation in which first a reaction solvent is prepared, and then one or more compounds selected from the compounds each having a hydroxyl, thiol or amino group and a long chain N-acyl acidic amino acid anhydride are continuously fed at the same time. The reaction solution in the stirring vessel in which a prescribed amount of ingredients have been reacted can be provided for the next step, that is, the acid-precipitation and layer-separation step. When feeding a long chain N-acyl acidic amino acid anhydride into the stirring vessel, the anhydride may be in the form of a powder or a solid, or in the form of a solution of the powder or the solid in an inert organic solvent capable of dissolving the same or in the form of a slurry of the powder or solid dispersed in an inert organic solvent.

A compound having m functional groups of one kind or more, which are selected from the group consisting of hydroxyl, thiol and amino groups which are used in the reaction step of the production method of this invention are compounds that have a straight-chain, branched-chain or cyclic-chain hydrocarbon chain of molecular weight of 1,000,000 or less, which contains or does not contain an aromatic hydrocarbon, and optionally have substituents other than hydroxyl, thiol and amino groups. As such compounds, compounds having a compound residue such as the above described X can be used. The compound having m functional groups of one kind or more, which are selected from the groups consisting of hydroxyl, thiol and amino groups is preferably a compound with 1 to 40 carbon atoms. It is preferable that such compounds independently have, per molecule, at least one carboxyl group, sulfonic acid group, sulfate ester group, phosphate ester group or a salt thereof, as a substituent(s) other than hydroxyl, thiol and amino groups, because with such compounds, the acyl group-containing composition of this invention excels in solubility in a weak-acid solution.

In the reaction step of the production method of this invention, usually preferably the molar ratio of the total functional groups contained in one kind or more compounds having, per molecule, m functional groups of one kind or more selected from the group consisting of hydroxyl, amino and thiol groups to a long chain N-acyl acidic amino acid anhydride is 0.1 to 5. To produce an acyl group-containing composition of high purity with the least possible separation and purification treatment after the reaction, it is preferable to carry out the reaction in the molar ratio range of 0.5 to 2, though its depends on the purpose for which the acyl group-containing composition of this invention is used. If the molar ratio is less than 0.5, the anhydride shows more tendency towards hydrolysis, which leads to an increase in the ratio of the long chain N-acyl acidic amino acid formation. On the other hand, if the molar ratio is higher than 2, the amount of the compounds having a hydroxyl, thiol or amino group that remain unreacted tends to be increased, and such impurities require separation and purification treatment depending on the purpose for which the acyl group-containing composition of this invention is used. The molar ratio is more preferably in the range of 0.6 to 1.4 and much more preferably 0.75 to 1.15.

When employing the acid-precipitation and layer-separation step in the production method of this invention, the pH of the reaction solution obtained in the above described reaction step is adjusted to 1 to 6 by adding a mineral acid such as hydrochloric acid or sulfuric acid to the solution, thereby separating the reaction solution into two layers, an organic layer and a water layer, allowing to obtain the organic layer, which includes an acyl group containing composition. In the reaction solution, part of or all of the acyl group-containing composition formed exists in the form of an alkaline salt. Addition of a mineral acid allows part of or all of the carboxyl groups in the acyl group-containing composition to be free acid, thereby separating the reaction solution into an organic layer and a water layer. In this process, inorganic salts, which are water-soluble impurities, and unreacted compounds each having a hydroxyl, thiol or amino group move to the water layer, thereby being removed from the acyl group-containing composition.

In the acid-precipitation and layer-separation step, it does not matter whether an organic solvent is present or not. However, the presence of an organic solvent makes the layer separation more likely to occur, and therefore it is preferable to carry out the step in the presence of an organic solvent. For example, when the reaction in the reaction step is carried out with an aqueous solvent alone, an organic solvent is added in the acid-precipitation and layer-separation step. Although the content of the organic solvent at the time of the acid-precipitation and layer-separation may be determined arbitrarily, the content in the mixed solution is preferably 0.01 to 99% by weight.

When using an organic solvent in the above described reaction step, the organic solvent may be used at the time of the acid-precipitation and layer-separation as well. Other organic solvents such as methanol, ethanol, propanol, isopropanol, butanol and isobutanol may also be used. Two kinds or more of these solvents can be used in combination. In the following, the acid-precipitation and layer-separation step will be described in detail in terms of a system where tertiary butanol alone is used as a preferable hydrophilic organic solvent.

The dissociation state of carboxyl group changes depending on the pH of the reaction solution at the time of acid-precipitation and layer-separation. And the state of layer-separation, in other words, the weight ratio of the organic layer to the water layer or the removability of inorganic salts, changes a little with the change of the dissociation state of carboxyl group. Accordingly, preferably the reaction is carried out in the pH range of 1 to 3 and more preferably in the pH range of 1 to 2.5.

The temperature at the time of acid-precipitation and layer-separation is preferably in the range of 35° C. to the boiling point of the hydrophilic organic solvent used. For example, when the hydrophilic organic solvent is tertiary butanol, preferably the temperature is in the range of 35° C. to 80° C. and more preferably in the range of 40° C. to 70° C. The reason of this is that if the temperature is lower than 35° C., it takes a longer time for the system to attain layer-separation equilibrium. Or even if the system attains layer-separation equilibrium, a considerable amount of inorganic salts can sometimes remain in the organic layer, or layer separation cannot sometimes occur depending on the types of the acyl group-containing composition or its concentration in the reaction solution. On the other hand, a temperature higher than 80° C. is also disadvantageous, because if the temperature is higher than 80° C., boiling is more likely to occur since the boiling point of the azeotropic composition of water/tertiary butanol is near 80° C. at a normal pressure.

When employing a washing step in the production method of this invention, the washing step, which is mainly intended to remove impurities the acid-precipitation and layer-separation step cannot remove, may be carried out without the acid-precipitation and layer-separation step. Specifically, the acyl group-containing composition, tertiary butanol and water are mixed so as to give a composition which can be separated into two layers, an organic layer and a water layer, and then water-soluble impurities, mainly inorganic salts or unreacted compounds each having a hydroxyl, thiol or amino group, in the organic layer which includes the acyl group-containing composition are moved to the water layer by solvent extraction. Just like the above described acid-precipitation and layer-separation step, the step will be described in detail in terms of a system where tertiary butanol alone is used as a hydrophilic organic solvent.

The present inventors have found that a mixed solution of an acyl group-containing composition of this invention/tertiary butanol/water is separated into two layers, an organic layer that contains the acyl group-containing composition, and a water layer, if only the composition of the mixed solution is adjusted so that it falls in a specified range. They have also found that the above layer separation makes it possible to remove the inorganic salts or unreacted compounds, each having a hydroxyl, thiol or amino group, in the organic layer. Specifically, if water and/or tertiary butanol is added to the organic phase formed in the acid precipitation and layer separation step so as to give a composition in which layer separation occurs, or tertiary butanol and/or water is added to the acyl group-containing composition that contains a large amount of impurities such as inorganic salts, layer separation occurs in the system, thereby making it possible to remove the inorganic salts etc, in the organic layer.

In both the acid-precipitation and layer-separation step and the washing step, the higher the tertiary butanol concentration of the layer separation region becomes, the shorter the time required for the layer separation of the system becomes. Accordingly, it is preferable to increase the concentration of tertiary butanol within the concentration range that permits layer separation. When employing the washing step, the washing temperature is 35 to 80° C. and preferably 40 to 70° C. for the same reasons having been described in terms of the acid-precipitation and layer-separation step.

To take out the acyl group-containing composition from the organic layer after layer separation, which contains only a decreased amount of water-soluble impurities such as inorganic salts, the organic solvent is removed from the organic layer by fractional distillation or by crystallization of the organic layer by acidification and cooling, followed by filtration.

The fractional distillation of the organic solvent may be carried out in accordance with conventional procedures using a stirring vessel, or it may be carried out using a thin film evaporator, such as a falling film evaporator, centrifugal thin film evaporator or agitated thin film evaporator, or using a spray evaporator. When removing the organic solvent by fractional distillation, the part of the carboxyl groups in the acyl group-containing composition may be neutralized or may not be neutralized before distilling off the solvent. However, the fractional distillation which involves neutralization of part of the carboxyl groups in the acyl group-containing composition is preferable in that once the organic solvent is removed, a neutralized aqueous solution of the acyl group-containing composition can be obtained directly.

Since solutions including an acyl group-containing composition are foamable, it is not easy to carry out distillation efficiently on an industrial scale while inhibiting the foaming of solutions. In this respect, distillation using a spray evaporator can be carried out efficiently even on an industrial scale. From that point of view, the process using a spray evaporator is preferable.

The distillation with a spray evaporator is to evaporate a solvent using, for example, an apparatus disclosed in JP-B-7-51201 in the following steps: draining a solution from the bottom of an evaporator can; circulating the solution to a heat exchanger by using a pump to overheat it to a prescribed extent; spraying the overheated solution in the inside of the can through piping provided on the top of the can. This method has the following characteristics: (1) in the gas phase portion of the evaporator can, one or more nearly cylindrical tube tip is provided with its end facing the solution surface and is connected to the piping provided on the top of the can; (2) the overheated solution having been passed through the heat exchanger is evaporated, until it reaches the tube tip, by controlling the flow rate of the solution in the heat exchanger and the overheated degree of the same at the outlet of the heat exchanger to obtain a gas-liquid two-phase flow; and (3) the amount of the overheat remaining in the solution droplets having been sprayed through the tube tip is released in the gas phase portion until the droplets reach the surface of the liquid phase in the evaporation can.

This method enables the production of an acyl group-containing composition of considerably low degree of coloration and of high purity.

The acyl compounds represented by the general formula (2) can be isolated from the acyl group-containing composition produced by the above described methods by properly adopting purification means known in the art.

The acyl group-containing composition of this invention contains an acyl compound at a purity of 70% by weight or more. If the purity is low, the efficiency of the composition as a surfactant is decreased, or the desired physical properties of the acyl group-containing composition of this invention can sometimes be impaired. Further preferably, the purity of the acyl compound is 85% by weight or more.

The acyl group-containing composition of this invention contains only a trace amount of dehydrated acyl compound product derived from an acyl compound, and preferably the content is 5% or less in terms of its area ratio to the acyl compound which is obtained by the analysis by high performance liquid chromatography using a detector at 205 nm. The dehydrated acyl compound is very hard to separate from the acyl compound, and once the dehydrated acyl compound is formed, it is very difficult to remove it completely by purification. When the acyl group-containing composition is used in the form of an aqueous solution, the lower the content of the dehydrated acyl compound, the less the turbidity or coloration of the aqueous solution. Thus, the content is preferably 3% or less and more preferably 1% or less (based on the above described analytical method).

The acyl group-containing composition of this invention can be neutralized by a basic substance, and therefore it can be used as aqueous solutions having a wide pH region if its neutralization rate is adjusted. Preferably, the acyl group-containing composition is used in such a state that 0.2 to 2 equivalent of 1 equivalent of its dissociated group (carboxyl group) is neutralized (i.e., neutralization rate is 0.2 to 2).

Preferably, the acyl group-containing composition of this invention is such that when it is neutralized with, for example, sodium hydroxide and prepared into a 20% by weight aqueous solution of pH 10, the transmittances both at 430 nm and at 550 nm are 90% or more. Since occurrence of turbidity or coloration in its aqueous solution lowers its value as a commercial product, it is preferable that either one of the transmittances is 90% or more and more preferably 95% or more.

The acyl group-containing composition of this invention can be used directly as a surfactant depending on the application for which the surfactant is used and can also be used in the form of an aqueous solution. The composition can sometimes be hard to handle as a solid at ordinary temperature depending on its properties. In such a case, preferably it is handled in the form of an aqueous solution. For example, aqueous solutions containing the acyl group-containing composition can have a pH ranging from 3 to 12. Preferably the pH of the aqueous solutions is adjusted to 4.5 to 11. The aqueous solutions prepared as above are less irritating to the skin and have remarkably excellent surface activity even at low concentrations. More preferably, the pH of the aqueous solutions is adjusted to 5 to 8.

When the acyl group-containing composition of this invention is used in the form of a solution, the content of the acyl group-containing composition is not particularly limited. The content can be 0.01 to 99% by weight and preferably 0.01 to 50% by weight, which is within the range that allows the composition to exert surface activity, depending on the application for which it is used.

The aqueous solution containing the acyl group-containing composition may contain another surfactant, such as an anionic, nonionic, cationic or amphoteric surfactant, depending on the situation. Above all, those containing a long chain N-acyl amino acid or a salt thereof as an anionic surfactant in the aqueous solution in such an amount that (A) an acyl group-containing composition and (B) a long chain N-acyl amino acid or the salt thereof are contained in the mass ratio (A)/(B) of 1/100 to 100/1 in the aqueous solution are preferable.

The term "long chain N-acyl amino acid" herein used means an amino acid with an acyl group derived from a saturated or unsaturated fatty acid with 8 to 20 carbon atoms introduced to its amino group. The amino acid residue in the long chain N-acyl amino acid may be an α-amino acid, β-amino acid, γ-amino acid or ω-amino acid and the amino group may be a N-methyl group or N-ethyl group. It does not matter which optically isomeric configuration the acidic amino acid has. It may be a D-isomer, L-isomer or racemate.

Examples of such amino acids include glutamic acid, asparagic acid, glycine, alanine, lanthionine, β-methyl-lanthionine, cyctathionine, diencholic acid, felinine, aminomalonic acid, β-oxyasparagic acid, α-amino-α-methyl-succinic acid, β-oxyglutamic acid, γ-oxyglutamic acid, γ-methylglutamic acid, γ-methyleneglutamic acid, γ-methyl-γ-oxyglutamic acid, α-aminoadipic acid, α,α'-diaminoadipic acid, β,β'-diaminoadipic acid, α-amino-γ-oxyadipic acid, α-aminopimelic acid, α-amino-γ-oxypimelic acid, β-aminopimelic acid, α-aminosuberic acid, α-aminosebacic acid and pantothenic acid.

The acyl group may be any acyl group as long as it is derived from a saturated or unsaturated fatty acid with 8 to 20 carbon atoms. It does not matter whether it is a straight-chain, branched-chain or cyclic-chain. From the viewpoint of biodegradability, it is preferable that the a long chain N-acyl amino acid is a long chain N-acyl-L-amino acid.

Typical examples of applications for which the acyl group-containing composition of this invention or aqueous solutions thereof are used are: raw materials for industrial cleaning agents and treatments, domestic detergents (for clothes, kitchen, house, tableware, etc.), cosmetics, foods, medicines, emulsifying (polymerization) agents, agricultural chemicals, textile processing agents (scouring agent, dye-assist agent, textile softener, water repellent), stainproofing agents, concrete admixtures, printing inks, lubricating oils, antistatic agents, anti-fogging agents, lubricants, dispersants and deinking agents.

These are useful applications where the characteristics of this invention, such as less coloration in products, less irritation to the skin, surface activity at low concentrations, moisturizing performance, pigment dispersion stability, detergency, high emulsifying stability, low loading on environment due to biodegradability, are made good use of. When using the acyl group-containing composition of this invention for these applications, it is prepared into formulas (e.g. cosmetic compositions) depending on the applications for which it is used. The amount of the acyl group-containing composition blended in a formula is not particularly limited, and it can be in the range of 0.01 to 99% by weight and preferably in the range of 0.01 to 50% by weight depending on the application. The acyl group-containing composition of this invention can be used as solutions having a pH, for example ranging widely from 3 to 12, preferably as solutions having a pH ranging from 4.5 to 11 and more preferably as solutions having a pH ranging from 5 to 8 by adjusting the neutralization rate of the composition with a basic substance.

When using the acyl group-containing composition of this invention as formulas for various applications, it can take the form of a liquid, a solid, a gel, a paste or a mist depending on the purpose for which it is used.

The acyl group-containing composition of this invention and the aqueous solution thereof are used as materials for cosmetics.

The term "cosmetics" herein used indicates the general term of quasi drugs and cosmetics stipulated in Pharmaceutical Affairs Law. Specifically, examples of quasi drugs include mouth refrigerants, underarm deodorants, talcum powders, hair growth stimulants, hair removers, hair dye, permanent wave preparations, bath preparations, medicated cosmetics and medicated dentifrice. Examples of cosmetics include: cleansing cosmetics such as toilet soaps, facial cleansing agents (in the cream/paste, liquid/gel, granule/powder, or aerosol form), shampoos and rinses; hair care cosmetics such as dyes, hair treatments (in the form of cream, mist, oil, gel and others, including split hair coating preparations), hair setting preparations (hair oils, hair setting lotions, curler lotions, pomade, stick pomade, bintsuke (hair setting) oil, hair spray, hair mist, hair liquid, hair foam, hair gel, water grease); basic cosmetics such as general skin cream, milky lotion (e.g. cleansing cream, cold cream, vanishing cream, hand cream), shaving creams (e.g. after shaving cream, shaving cream), skin lotions (e.g. hand lotions, general skin lotions), eau de colognes, shaving lotions (e.g. after shaving lotion, shaving lotion), cosmetic oils and face packs; makeup cosmetics such as face powders (cream powder, pressed powder, powder, talcum powder, grease paint, baby powder, body powder, liquid powder), powder, foundation (cream, liquid, solid, etc.), cheek colors, eyebrow color, eye cream, eye shadow and mascara; perfumes such as general perfumes, grease perfumes and powder perfumes; fragrance preparations of gel, liquid or ceramic containing potpourri type, deodorants and deodorizers; suntan/sunscreen cosmetics such as suntan/sunscreen creams, suntan/sunscreen lotions and suntan/sunscreen oils; manicure preparations such as nail cream, nail enamel and nail enamel remover; eye liners; lip cosmetics such as lip stick and lip cream; mouth preparations such as dentifrices; and bath preparations such as bath salts, bath oils and bubble baths. Among them, the formulas of the acyl group-containing composition of this invention are often used as materials for cleansing cosmetics, hair care cosmetics and basic cosmetics, and particularly suitably used as materials for cleansing cosmetics.

When using the acyl group-containing composition of this invention as cosmetic compositions, preferably the cosmetics include one or more the acyl group-containing compositions and a polyhydroxyl compound.

Examples of polyhydroxyl compounds, which have 2 or more hydroxyl groups per molecule, include: divalent hydroxyl compounds such as ethylene glycol, 1,2-propanediol, 1,3-propanediol, 1,2-butanediol, 1,3-butanediol, 1,4-butanediol, pentanediol, 1,6-hexanediol, cyclohexanediol, dimethylolcyclohexane, neopentyl glycol, 1,8-octanediol, 2,2,4-trimethyl-1,3-pentanediol, isoprene glycol, 3-methyl-1,5-pentanediol, sorbite, catechol, resorcin, hydroquinone, bisphenol A, bisphenol F, hydrogenated bisphenol A, hydrogenated bisphenol F, dimerdiol, dimethylolpropionic acid, dimethylolbutanoic acid, tartaric acid, dihydroxytataric acid, mevalonic acid, 3,4-dihydroxycinnamic acid, 3,4-dihydroxyhydrocinnamic acid, hydroxybenzoic acid, dihydroxystearic acid, dihydroxyphenylalanine and the isomers thereof; trivalent polyhydroxyl compounds such as glycerol, trioxyisobutane, 1,2,3-butanetriol, 1,2,3-pentanetriol, 2-methyl-1,2,3-propanetriol, 2-methyl-2,3,4-butanetriol, 2-ethyl-1,2,3-butanetriol, 2,3,4-pentanetriol, 2,3,4-hexanetriol, 4-propyl-3,4,5-heptanetriol, 2,4-dimethyl-2,3,4-petanetriol, 1,2,4-butanetriol, 1,2,4-pentanetriol, trimethylolethane, trimethylolpropane, diethanolamine, triethanolamine, trihydroxystearic acid; tetravalent polyhydroxyl compounds such as pentaerythritol, erythritol, 1,2,3,4-pentanetetrol, 2,3,4,5-hexanetetrol, 1,2,4,5-pentanetetrol, 1,3,4,5-hexanetetrol, diglycerol and sorbitan; pentavalent polyhydroxyl compounds such as adonitol, arabitol, xylitol and triglycerol; hexavalent polyhydroxyl compounds such as dipentaerythritol, sorbitol, mannitol, iditol, inositol, dalsitol, talose and allose; the dehydration condensation products thereof; and polyglycerols.

Examples of such polyhydroxyl compounds also include saccharides: for example, monosaccharides, such as tetrose such as erythrose, threose and erythrulose, pentose such as ribose, arabinose, xylose, lyxose, xylulose and ribulose, hexose such as allose, altrose, glucose, mannose, gulose, idose, galactose, tarose, fructose, sorbose, psicose and tagatose; and oligosaccharides such as maltose, isomaltose, cellobiose, gentiobiose, meribiose, lactose, turanose, treharose, saccharose, mannitriose, cellotriose, gentianose, raffinose, melezitose, cellotetrose and stachyose.

Such polyhydroxyl compounds may be other saccharide residues such as heptose, deoxy-saccharides, amino-saccharides, thio-saccharides, seleno-saccharides, aldonic saccharides, uronic acid, sugar acid, ketaldonic acid, anhydrosugars, unsaturated sugars, sugar esters, sugar ethers and glycoside, or polysaccharides such as starch, glycogen, cellulose, chitin and chitosan, or hydrolyzed products thereof. The combination of two kinds or more of these polyhydroxyl compounds may also be used. Preferable polyhydroxyl compounds are those with valence of 3 or more.

Preferably, the cosmetics containing the acyl group-containing composition of this invention contain one kind or more acyl group-containing compositions and a polyhydroxyl compound, wherein the content of the polyhydroxyl compound is 0.001 to 40% by weight and the content of the acyl group-containing composition is 10/1 to 1/100 in terms of the weight ratio to the polyhydroxyl compound. If the content of the polyhydroxyl compound is less than 0.001% by weight, the cosmetics leave the skin feeling less moist and the moisturizing effect of the composition is hard to exert, whereas if the content of the polyhydroxyl compound is higher than 40% by weight, the cosmetics leave the skin feeling stickier. If the amount of the acyl group-containing composition is less than 1/100 in terms of the weight ratio to the polyhydroxyl compound, the cosmetics are likely to give users feeling of stickiness coming from the polyhydroxyl compound and other ingredients, whereas if the amount is more than 10/1, the cosmetics are likely to give users feeling of stickiness coming from the acyl group-containing composition. More preferably, the content of the polyhydroxyl compound is 0.1 to 30% by weight and the content of the acyl group-containing composition is 5/1 to 1/50 in terms of the weight ratio to the polyhydroxyl compound. Much more preferably, the content of the acyl group-containing composition is 5/1 to 1/20 in terms of the weight ratio to the polyhydroxyl compound.

In the cosmetics containing the acyl group-containing composition of this invention, use of oil ingredients is preferable, because they provide moisturizing and emollient effects on the skin. As oil ingredients, either liquid oil or solid fat may be used and those commonly used as ingredients for cosmetics or medicines for external application may also be used.

Examples of oil ingredients include volatile and non-volatile ones, specifically they include: oils and fats such as avocado oil, almond oil, olive oil, cacao oil, sesame oil, safflower oil, soybean oil, camellia oil, persic oil, castor oil, grape seed oil, macadamia nut oil, mink oil, cottonseed oil, Japan tallow, coconut oil, yolk oil, palm oil, palm stone oil, glyceryl triisooctanoate, glyceryl tri-2-ethylhexanoate and cholesterol fatty acid ester; waxes such as spermaceti, carnauba wax, candellia wax, jojoba seed oil, bee wax, lanolin and the derivatives thereof; hydrocarbons such as liquid paraffin, paraffin, vaseline, ceresin, microcrystalline wax, squarane and squalene; higher fatty acids such as lauric acid, myristic acid, palmitic acid, stearic acid, isostearic acid, oleic acid, behenic acid, undecylenic acid, lanolin fatty acid, hard lanolin fatty acid and soft lanolin fatty acid; higher alcohols such as lauryl alcohol, cetyl alcohol, cetostearyl alcohol, stearyl alcohol, isostearyl alcohol, 2-octyldodecanol, oleyl alcohol, behenyl alcohol, lanolin alcohol, hydrogenated lanolin alcohol and hexyldecanol; higher alcohol fatty acid esters such as isopropyl myristate, octadecyl myristate, 2-octyldodecyl myristate, cetyl 2-ethylhexanoate, diisostearyl malate, isostearyl isostearate, isostearyl cholesteryl ester and butylstearate; and silicone oils such as (di)methyl silicone, methyl phenyl silicone, amino modified silicone and cyclic silicone. These oil ingredients may be used in combination of two kinds or more.

Cosmetics that contain the acyl group-containing composition of this invention can be produced by mixing, while stirring, an acyl group-containing composition, a polyhydroxyl compound and, if necessary, water and an oil ingredient. Particularly when producing an oil ingredient-containing emulsion such as a milky lotion, a later-described process is preferably used in which cosmetics are produced by emulsifying an acyl group-containing composition, a polyhydroxyl compound and an oil- and gelatinous-composition that contains an oil ingredient.

Specifically, oil- and gelatinous-compositions are very easily brought to the stable emulsified and dispersed state when they are stirred with water added thereinto; and therefore, cosmetics are produced only by adding water to oil- and gelatinous-compositions. To produce cosmetics that further excel in a moist feeling or moisture retaining effect and are in the stable emulsified state, a process is preferable in which not only water, but also a polyhydroxyl compound, a higher alcohol or oil ingredients are properly added to the above described gelatinous composition depending on the situation.

The cosmetics that contain the acyl group-containing composition of this invention obtained as above are characterized by excellent moist feeling, excellent moisture retaining effects and being capable of keeping a very stable emulsified state over time.

Cosmetics that contain the acyl group-containing composition of this invention can be applied to, for example, a milky lotion, a cream, a lotion and a skin lotion, along with those intended to cleanse the skin, such as a cleansing lotion, a facial cleansing preparations and a body shampoo. Cosmetics that contain the acyl group-containing composition of this invention can take various forms such as a liquid, a paste, a gel and an aerosol, depending on desire.

When using the acyl group-containing composition of this invention as a blended composition, preferably the composition is used as a gelatinous composition that contains the acyl group-containing composition, a polyhydroxyl compound and oil ingredients.

Examples of polyhydroxyl compounds having 2 or more hydroxyl groups per molecule and applicable to the gelatinous composition of this invention include those described above. In the gelatinous composition of this invention, polyhydroxyl compounds with valency of 3 or more are preferably used.

Polyhydroxyl compounds may be used in combination of two kinds or more and polyhydroxyl compounds with different valencies, for example, polyhydroxyl compounds of 2-valency and 3-valency may also be used in combination.

Examples of oil ingredients used in the gelatinous composition of this invention include those described above.

The gelatinous composition of this invention contains one kind or more acyl group-containing compositions, one or more polyhydroxyl compounds having 2 or more hydroxyl groups per molecule and one or more oil ingredients, and preferably the water content in the gelatinous composition is 50% by weight or less and the composition of the gelatinous composition is such that 1) the total amount of acyl group-containing composition(s) is 0.1 to 40% by weight, 2) the total amount of polyhydroxyl compound(s) is 1 to 60% by weight and 3) the total amount of oil ingredient(s) is 1 to 95% by weight. The contents of acyl group-containing compositions, polyhydroxyl compounds and oil ingredients herein mentioned each indicate the total sum of the respective ingredients. If the water content is outside this range, the gel state of the composition cannot sometimes be kept stable. The water content is more preferably 30% by weight or less and much more preferably 20% by weight or less.

Even if the content of each ingredient is outside the above described range, the composition can sometimes take the gel form. However, such gelatinous composition can sometimes be poor in stability due to the separation of oil ingredients, be poor in gel forming performance, have decreased detergency, or have an unfavorable after feel depending on the purpose for which it is used.

In the gelatinous composition of this invention that contains an acyl group-containing composition(s), the composition of acyl group-containing composition(s), polyhydroxyl compound(s) and oil ingredient(s) is more preferably such that 1) the total amount of surfactant(s) is 1 to 25% by weight, 2) the total amount of polyhydroxyl compound(s) is 5 to 40% by weight and 3) the total amount of oil ingredient(s) is 20 to 80% by weight and much more preferably 1) the total amount of surfactant(s) is 3 to 15% by weight, 2) the total amount of polyhydroxyl compound(s) is 5 to 30% by weight and 3) the total amount of oil ingredient(s) is 30 to 70% by weight.

In the production of the gelatinous composition of this invention, to obtain one whose appearance is transparent, it is preferable to allow the difference in refractive index at 20° C. between the water phase, which is composed of an acyl group-containing composition(s), a polyhydroxyl compound(s) and water, and the oil phase, which is composed of an oil ingredient(s), to be ±0.05 or less. If the difference in refractive index between the two phases is outside the range, one whose appearance is transparent cannot be obtained. The closer the difference in refractive index between the two phases comes to 0, the better. More preferably the difference is ±0.03 or less and much more preferably 0.01 or less. It is particularly preferable that the difference is 0.

The gelatinous composition of this invention is produced by mixing, while stirring, an acyl group-containing composition(s), a polyhydroxyl compound(s), an oil ingredient(s) and, depending on the situation, water under high shear stress. A preferred production process is to fully mix, while stirring, the ingredients other than the oil ingredient(s) and then add the oil ingredient(s) to the mixture little by little.

The gelatinous composition of this invention obtained as above has excellent characteristics of: 1) being highly capable of forming a gelatinous composition and keeping a stable gel state over time, 2) having a wide range of viscosity, 3) being easily fine-dispersed and brought to an emulsion state when water is added, and 4) being easily washed with water when used as a cleansing agent such as a cleansing preparation and leaving no residue on the skin while leaving the skin feeling refreshed.

Typical examples of suitable applications of the gelatinous composition of this invention are: various external preparations, gel base materials, and cleaners. Examples of external preparations include: various kinds of cosmetics such as a cream or a gel for facial washing/cleansing, a cold cream, a vanishing cream or a moisturizing cream; skin or hair care cosmetics such as massage gel and hair dressings; and drugs such as antiphlogistics or gelatinous pharmaceuticals, or vermin repellent. Examples of inclusion/carrier type of gel base materials include: sustained-release perfume gels in which perfume or an absorbent/adsorbent such as activated carbon is included/dispersed; deodorizing gel base materials; and in addition, pesticides and bath agents in which the water-dispersibility of the materials is made good use of. The gelatinous composition of this invention can also be used as cleaners, in which its characteristic of absorbing oil ingredients is made good use of, such as cleaners for oil stains in the kitchen and around gas ranges, cleaners for oil stains on machines, cleaners for hands, and cleaners for coated surfaces on metals of cars etc., coated surfaces on woods of family Buddhist altars/Buddhist altar fittings/wardrobes/desks, etc., plastic surfaces of electric appliances such as TVs/personal computers and glass surfaces.

When used for cleansing agents the gelatinous composition that contains the acyl group-containing composition of this invention, those whose viscosity at 25° C. is in the range of 1000 to 200000 mPa·s are preferably used because they spread smoothly when applied to the skin etc. The gelatinous compositions whose viscosity at 25° C. is in the range of 3000 to 60000 mPa·s are more preferably used When using the acyl group-containing composition of this invention as a blended composition, preferably it is used as a dispersant composition that contains the acyl group-containing composition.

The dispersant composition that contains the acyl group-containing composition of this invention prevents hydrophilic and/or hydrophobic powder from aggregating, and therefore, excels in dispersion stability. Such a dispersant composition can be used with various pigments in the following application fields, specifically including, pigments in the water-based/non-water-based coating fields; those in the pigment/printing ink fields, such as titanium white, red iron oxide, aluminum powder, talc, carbon black, azo pigment and phthalocyanine, those in the pigment/cosmetic fields (including bath agents), such as carbon black, azo pigment and phthalocyanine; those in the pigment/reinforced rubber, plastic fields, such as talc, (fine-grained) titanium oxide, titanium, mica, alumina, bentonite, red iron oxide, zinc laurate, zinc stearate, zinc oxide, chromium oxide, ultramarine, Prussian blue, iron oxide, kaolin, sericite, safflower pigment and cochineal extract; those in pigment/fiber, dyeing fields, such as clay, calcium carbonate, silica, carbon black and phthalocyanine; pigment printing, disperse dye/cement, concrete fields; cement/coated paper coating color fields; pigment/optical catalyst fields, such as calcium carbonate, talc, titanium oxide and clay; and ultra fine particle titanium oxide. Examples of other pigments include: inorganic pigments such as cobalt blue, chromium green, chromium oxide, silicic acid anhydride and magnesium aluminate silicate; organic pigments such as powdered skin of fruits or nuts, powdered Japanese cypress, polyethylene powder, polymethylsilsesquioxane powder, Hansa yellow, benzidine yellow, permanent yellow, tartrazine lake, quinone yellow, Sudan 1 and permanent orange; metal powder pigments such as bronze powder; inorganic fluorescent pigments such as zinc sulfide, zinc silicate, zinc cadmium sulfide, calcium sulfide, strontium sulfide and calcium tungstate; and other known organic fluorescent pigments.

The dispersant composition that contains the acyl group-containing composition of this invention may or may not contain water. It may take the form of a solid, a liquid or a paste which is simply a mixture of the acyl group-containing composition, a pigment, etc. It can be used in the form of: pigment coated with the acyl group-containing composition; pigment to which the acyl group-containing composition is sealed using a polymer etc. as a matrix; pigment bearing the acyl group-containing composition; or pigment chemically binding to the acyl group-containing composition directly or via a crosslinking agent or the like.

In the dispersant composition that contains the acyl group-containing composition of this invention, preferably the percentage of the acyl group-containing composition to a pigment is 0.01% by weight or greater, more preferably 0.1% by weight or greater, and much more preferably 1% by weight or greater. A larger percentage of the acyl group-containing composition to the pigment in the dispersant composition makes the dispersant composition more stable, as long as there is no other problem. However, if the amount exceeds 500% by weight, there can sometimes be created problems depending on the application; for example, when the dispersant composition is applied to ink, the water resistance of the ink can sometimes deteriorate.

A pigment dispersant can be produced with the dispersant composition of this invention by mixing, while stirring, the dispersant composition, a pigment and a dispersion medium with a dispersion mixer commonly used such as a ball mill, roll mill, sand mill, flow mill, dyno-mill, attritor, homomixer, homogenizer or high-speed disperser. The mixing while stirring can be carried out at an ordinary temperature or with heating, depending on the situation.

The acyl group-containing composition of this invention is also useful for cleansing agent compositions. With the acyl group-containing composition of this invention, a cleansing composition can be provide which is capable of decreasing surface tension even at low concentrations, is less irritating to the skin, and excels in forming properties and a refreshing afterfeel. The acyl group-containing composition of this invention is characterized in that when it is dissolved in water to prepare a dilute aqueous solution and used to wipe sebum off one's face, it leaves the face skin feeling smooth. Further, because the composition itself has a moisture retention performance, it can be used a moisturizer.

The acyl group-containing composition of this invention can be used together with various kinds of base materials depending on the application and purpose for which it is used.

Specifically, the acyl group-containing composition of this invention can be used together with:

a dispersant such as netural gum, such as gum arabic or traganth gum, glucoside, such as saponin, cellulose derivatives such as methyl cellulose, carboxy cellulose or hydroxymethyl cellulose, natural polymer, such as lignin sulfonate or shellac, anionic polymer, such as polyacrylate, salt of styrene-acrylic acid copolymer, salt of vinylnaphthalene-maleic acid copolymer, sodium salt or phosphate of β-naphthalenesulfonic acid formalin condensation product or nonionic polymer, such as polyvinylalcohol, polyvinylpirrolidone or polyethylene glycol;

an anionic surfactant such as a fatty acid salt (soap), alkylsulfonic acid ester salt (AS), polyoxyethylenealkyl ether sulfate ester salt (AES), α-olefin sulfonat (AOS), alkylbenzene sulfonate, alkylnaphthalene sulfonate, alkyl sulfonate (SAS), dialkyl sulfosuccinate, α-sulfonated fatty acid salt, long chain N-acyl amino acid salt, N-acyl-N-methyl taurinate, sulfated fat and oil, polyoxyethylene styrenated phenylether sulfate, alkyl phosphate, polyoxyethylene alkyl ether phosphate, polyoxyethylene alkyl phenyl ether phosphate or naphthalene sulfonate formalin condensation product;

an amphoteric surfactant such as an alkyl betaine, alkyl amide betaine, alkyl sulfo betaine or imidazolinium betaine;

a nonionic surfactant such as fatty acid alkylol amide, alkyl amine oxide, polyoxyethylene alkyl ether (AE), polyoxyethylene alkyl phenyl ether, polyoxyethylene polystyryl phenyl ether, polyoxyethylene polyoxypropylene glycol, polyoxyethylene polyoxypropylene alkyl ether, polyhydric alcohol fatty acid partial ester, polyoxyethylene polyhydric alcohol fatty acid partial ester, polyoxyethylene fatty acid ester, polyglycerol fatty acid ester, polyoxyethylene hardened castor oil, polyoxyethylene alkyl amine or triethanol amine fatty acid partial ester;

a cationic surfactant such as primary to tertiary fat amine salt, alkyl ammonium chloride salt, tetraalkyl ammonium salt, trialkyl benzyl ammonium salt, alkyl pyridinium salt, alkyl hydroxyethyl imidazolinium salt or dialkyl morpholinium salt;

a polymer surfactant such as sodium alginate, starch derivative or gum tragacanth;

a natural surfactant lecithin, lanolin, cholesterol or saponin;

a fatty and oil such as avocado oil, almond oil, olive oil, cacao oil, sesame oil, safflower oil, soybean oil, camellia oil, persic oil, castor oil, mink oil, cottonseed oil, Japan tallow, coconut oil, yolk oil, palm oil, palm stone oil, synthesized triglyceride or jojoba oil;

a hydrocarbon such as liquid paraffin, vaseline, ceresin, microcrystalline wax or isoparaffin;

a wax such as bees wax, spermaceti wax, lanolin, carnauba wax, candellia wax or a derivative thereof;

a higher fatty acid such as lauric acid, myristic acid, palmitic acid, stearic acid, isostearic acid, oleic acid, behenic acid, undecylenic acid, lanolin fatty acid, hard lanolin fatty acid or soft lanolin fatty acid;

a higher alcohol such as lauryl alcohol, cetanol, cetostearyl alcohol, stearyl alcohol, oleyl alcohol, behenyl alcohol, lanolin alcohol, hydrogenated lanolin alcohol and hexyldecanol or octyldecanol;

an ester oil such as isopropyl myristate, butyl stearate or others;

a volatile or nonvolatile oil such as metallic soap, or silicone oils such as straight silicone oil or modified silicone oil;

a polyol such as glycerol, diglycerol, polyglycerol, 1,3-butanediol, propanediol or polyethylene glycol;

a moisture retaining agent such as trimethylglycine, sorbitol, raffinose, pyrrolidone carboxylate, lactate, hyaluronate or ceramide;

a water- or oil-soluble polymer such as hydroxyethyl cellulose, carboxymethyl cellulose, hydroxyethyl cellulose hydroxypropyl trimethyl ammonium chloride ether, methyl cellulose, ethyl cellulose, hydroxypropyl cellulose, methyl hydroxypropyl cellulose, soluble starch, carboxymethyl starch, methyl starch, alginic acid propylene glycol ester, polyvinyl alcohol, polyvinyl pyrrolidone, polyvinyl methyl ether, carboxyvinyl polymer, polyacrylate, gum guar, locust bean gum, quince seed, carrageenan, galactan, gum arabic, pectin, mannan, starch, xanthane gum, dextran, suucinoglucan, curdlan, hyaluronic acid, gelatin, casein, albumin, collagen, methoxyethylene maleic anhydride copolymer, amphoteric methacrylate ester copolymer, poly dimethyl methylenepiperidium chloride, polyacrylate ester copolymer, polyvinyl acetate, nitrocellulose or silicone resin;

a thickening or lathering ingredient such as polyethylene glycol fatty acid ester, polyoxyethylene fatty acid ester methyl glycoside or tetradecene sulfonate;

a sequestering agent such as ethylenediamine tetraacetate or a salt thereof, hydroxyethylenediamine triacetate or a salt thereof, phosphoric acid, ascorbic acid, succinic acid, gluconic acid, polyphosphate, metaphosphate or hinokitiol;

a preservative such as paraoxybenzoate ester, benzoic acid or a salt thereof, phenoxyethanol or hinokithiel;

a pH adjustor such as citric acid, malic acid, adipic acid, glutamic acid or aspartic acid; and others such as an anti-dandruff/itching relief agent such as trichlorocarbanilide, salicylic acid, zinc pyrithione or iropropylmethylphenol an ultraviolet ray absorber such as benzophenone derivatives, paraminobenzoic acid derivatives, paramethoxycinnamic acid derivatives, salicylic acid derivatives or others;

a whitening agent such as albutin, kojic acid, ascorbic acid, hinokithiol and derivatives thereof;

a blood circulation improver such as swertia herb extract, cepharathine, vitamine E or a derivative thereof, or γ-oryzanol;

a local excitatory agent such as capsicum tincture, ginger tincture, cantharides tincture or benzyl nicotinate;

a nutrient such as various types of vitamins or amino acids;

a female hormone;

a hair root activating agent;

an antiinflammative such as glycyrrhizinic acid, glycyrrhizinic acid derivative, allantoin, azulene, aminocaproic acid or hydrocortisone;

an astringent such as zinc oxide, zinc sulfate, allantoin hydroxyaluminum, aluminum chloride, zinc sulfocarbolate or tannic acid;

a tonic such as menthol or camphor;

antihistamine;

an antioxidant such as silicone substance such as polymer silicone or cyclic silicone, tocopherols, BHA, BHT, gallic acid and NDGA; and purified water.

Particularly, the combination with fatty acid diethanol amide, polyoxyethylene methyl dioleate glucoside, distearate polyethylene glycol, tetradecene sulfonate, miristates or miristyldimethyl amine is useful in that it increases the viscosity and forming properties of the composition, and besides the combination with an amphoteric surfactant is very useful in that it further decreases irritation of the skin.

In the following this invention will be described in more detail giving examples and the like, which are not intended to limit this invention.

The evaluations used in the examples of this invention are as follows.

(A) Determination of acyl Compound, Dehydrated acyl Compound, Free Fatty Acid, and Long Chain N-acyl Acidic Amino Acid or the Salt thereof Ingredients were separated by high performance liquid chromatography (HPCL) over an ODS column (YMC-Pack, AM-312) using, as an eluent, a methanol/water/phosphoric acid system (methanol/1,4-dioxane/water/85% phosphoric acid=2450/60/490/1 (volume ratio)) and determination of the ingredients was carried out with an ultraviolet detector (SHIMADZU CORPORATION; SPD-10A) at 205 nm and a differential refractive index detector (SHIMADZU CORPORATION; RID-10A). Ingredients other than dehydrated acyl compounds were detected with the differential refractive index detector and dehydrated acyl compounds with the ultraviolet detector (because the amount of dehydrated acyl compounds existing was so small that it was hard to detect with a differential refractive index detector).

In the examples, the content of free fatty acid and that of long chain N-acyl acidic amino acid or the salt thereof were indicated in terms of % by weight to acyl compounds. Dehydrated acyl compounds were confirmed with an ultraviolet detector at 205 nm and their content was indicated by % by peak area to acyl group-containing compounds.

The term "purity of acyl group-containing composition" shown below means the percentage of the weight of acyl compound, as a product, to the total weight of acyl group-containing composition.

Evaluation criteria are as follows.

(Evaluation Criteria for Purity of Acyl Group-containing Composition)
Purity is 85% or more ◎
Purity is 70% to less than 85% ○
Purity is less than 70% x (Evaluation Criteria for Free Fatty Acid Content)
Content is 3% or more x
Content is 1% to less than 3% ○
Content is less than 1% ◎

(Evaluation Criteria for Dehydrated Acyl Compound Content)
Content is 5% or more x
Content is 1% to less than 5% ○
Content is less than 1% ◎

(Evaluation Criteria for Content of Long Chain N-acyl Acidic Amino Acid or the Salt Thereof)
Content is 15% or more x
Content is 1% to less than 10% ○
Content is less than 1% ◎

(B) Measurement of Transmittance of the Aqueous Solution

The transmittances at 430 nm and 550 nm were measured with a cell of optical path length 10 mm of a 20% by weight (pH 10) aqueous solution prepared by neutralizing an acyl group-containing composition with sodium hydroxide.

The evaluation criteria were as follows.
Transmittances both at 430 nm and at 550 nm are 95% or more ◎
Transmittances both at 430 nm and at 550 nm are 90% to less than 95% ○
Transmittances either of or both at 430 nm and at 550 nm are less than 90% Δ

(C) Stability of the Gelatinous Composition

Gelatinous compositions were kept at 40° C. and their state was observed after one month. The stability was evaluated for each composition in accordance with the following criteria.
○: The state is not changed and good
Δ: Separation is observed a little
x: Separation is apparent (D) Afterfeel of Gelatinous Composition Each gelatinous composition was applied to 5 panelists' hands and rubbed well into the skin to conduct a sensory test. And the afterfeel of each composition after washing the hands with water was evaluated in accordance with the following criteria.
○: The number of the panelists who feel that the composition does not leave the skin feeling sticky and has a good afterfeel is 3 or more
Δ: The number of the panelists who feel that the composition does not leave the skin feeling sticky and has a good afterfeel is 1 or 2
x: The number of the panelists who feel that the composition does not leave the skin feeling sticky and has a good afterfeel is 0

(E) Measurement of Viscosity

The viscosity of each gelatinous composition was measured at 25° C. with a B type viscometer (Brookfield; LVDVE115) and evaluated according to the following five ranks.

The viscosity of the gelatinous composition is 200,000 mPa or more

The viscosity of the gelatinous composition is 60,000 mPa or more and less than 200,000 mPa The viscosity of the gelatinous composition is 3,000 mPa or more and less than 60,000 mPa The viscosity of the gelatinous composition is 1,000 mPa or more and less than 3,000 mPa The viscosity of the gelatinous composition is less than 1,000 mPa (F) Ease of Spreading at the Time of Application Each cleansing agent was applied to 5 panelists to conduct a sensory test. And the ease of its spreading was evaluated according to the following criteria.
○: The number of the panelists who feel that the ease of spreading of the cleansing agent is good at the time of application is 3 or more
Δ: The number of the panelists who feel that the ease of spreading of the cleansing agent is good at the time of application is 1 or 2
x: The number of the panelists who feel that the ease of spreading of the cleansing agent is good at the time of application is 0

(G) Appearance

Each gelatinous composition was evaluated visually (based on "transparent", "translucent" or "separated").

(H) Measurement of Refractive Index

The refractive index of each phase at 20° C. was measured by a refractometer. The difference in refractive index between the oil phase and the water phase was evaluated according to the following 4 rank criteria.

The difference in refractive index between the oil phase and the water phase is 0.05 or more The difference in refractive index between the oil phase and the water phase is 0.03 or more and less than 0.05

The difference in refractive index between the oil phase and the water phase is 0.01 or more and less than 0.03

The difference in refractive index between the oil phase and the water phase is less than 0.01

(I) Stability of Cosmetics

Cosmetics were kept at 40° C. and their state was observed after one month. The stability was evaluated for each cosmetic in accordance with the following criteria.
○: The state is not changed and good
Δ: Separation is observed a little
x: Separation is apparent (J) Afterfeel of Cosmetics Each cosmetic was applied to 5 panelists' hands to conduct a sensory test. And the afterfeel of each cosmetic (sticky feeling, moist feeling) was evaluated in accordance with the following criteria.
○: The number of the panelists who feel that the cosmetic does not leave the skin feeling sticky, do leave the skin feeling moist and has a good afterfeel is 3 or more
Δ: The number of the panelists who feel that the cosmetic does not leave the skin feeling sticky, do leave the skin feeling moist and has a good afterfeel is 1 or 2
x: The number of the panelists who feel that the cosmetic does not leave the skin feeling sticky, do leave the skin feeling moist and has a good afterfeel is 0

In the following this invention will be described in detail giving examples.

EXAMPLE 1

(Reaction Step)

First, 9.1 g (0.05 mol) of L-lysine hydrochloride was mixed in 57 g of water. Then, 31.1 g (0.1 mol) of N-lauroyl-L-glutamic acid anhydride was added to the mixed solution under stirring over 2 hours, while adjusting the pH of the mixed solution in the range of 10 to 11 using a solution of 25% sodium hydroxide in water and keeping the reaction temperature at 5° C., to allow the reaction to progress.

(Acid-precipitation and Layer-separation Step)

After continuing another 30-minute stirring, tertiary butanol was added so that its concentration in the mixed solution was 20% by weight, and 75% sulfuric acid was added dropwise to adjust the pH of the solution to 2 while adjusting the temperature of the solution to 65° C. After completion of the sulfuric acid addition, stirring was stopped, and the mixed solution was left stand at 65° C. for 20 minutes so that the solution was separated into an organic layer and a water layer. Then the organic layer was isolated.

(Washing Step)

Tertiary butanol and water were added to the isolated organic layer to prepare a mixed solution having a composition of acyl compound/tertiary butanol/water=33/25/42 (% by weight). The mixed solution was stirred at 65° C. for 20 minutes. After stopping stirring, the mixed solution was left stand at 65° C. for 20 minutes so that the solution was separated into an organic layer and a water layer. Then the operation of washing the resultant organic layer with water was repeated to remove the solvent from the organic layer. Thus, 34.6 g of acyl group-containing composition was yielded. The analytical results are shown in Table 1.

EXAMPLE 2

The same steps as those of Example 1 were carried out under the same conditions except that in the reaction step, a mixed solution of water and tertiary butanol (concentration of tertiary butanol was 20% by weight) was used instead of water and N-lauroyl-D-glutamic acid anhydride was used instead of N-lauroyl-L-glutamic acid anhydride to yield 33.8 g of acyl group-containing composition. The analytical results are shown in Table 1.

EXAMPLE 3

The same steps as those of Example 1 were carried out under the same conditions except that in the reaction step, 7.2 g of octanediamine was used instead of 9.1 g of L-lysine hydrochloride, the reaction temperature was changed to 55° C. and the pH range to 11 to 12 to yield 32.9 g of acyl group-containing composition. The analytical results are shown in Table 1.

EXAMPLE 4

The same steps as those of Example 1 were carried out under the same conditions except that in the reaction step, 33.9 g of N-myristoyl-L-glutamic acid anhydride was used instead of 31.1 g of N-lauroyl-L-glutamic acid anhydride, the reaction temperature was changed to 15° C. and the pH range to 12 to 13 to yield 37.1 g of acyl group-containing composition. The analytical results are shown in Table 1.

EXAMPLE 5

The same steps as those of Example 1 were carried out under the same conditions except that in the reaction step, 31.1 g of N-cocoyl-L-glutamic acid anhydride was used instead of 31.1 g of N-lauroyl-L-glutamic acid anhydride and 3.0 g of ethylenediamine was used instead of 9.1 g of L-lysine hydrochloride to yield 29.0 g of acyl group-containing composition. The analytical results are shown in Table 1.

EXAMPLE 6

The same steps as those of Example 1 were carried out under the same conditions except that in the reaction step, 3.53 g of N-palmitoyl-L-asparagic acid anhydride was used instead of 31.1 g of N-lauroyl-L-glutamic acid anhydride and a mixed solution of water and toluene (concentration of toluene was 30% by weight) was used instead of water and 30° C. of the reaction temperature was used instead of 5° C. to yield 38.3 g of acyl group-containing composition. The analytical results are shown in Table 1.

COMPARATIVE EXAMPLE 1

Just like Example 9 described in JP-A-2002-167313, 31.1 g (0.1 mol) of N-lauroyl-L-glutamic acid anhydride was added to 400 mL of toluene and stirred at 95° C. Then, 3.7 g (0.05 mol) of 1,3-propanediamine was added dropwise to the mixed solution over 2 hours. After completing the addition of 1,3-propanediamine, the mixed solution was stirred 1 hour, and toluene was distilled off from the solution to obtain 33.1 g of an acyl group-containing composition. It was then purified by chromatography to yield 23.0 g of acyl group-containing composition. The analytical results are shown in Table 1.

COMPARATIVE EXAMPLE 2

The same operations as those of comparative Example 1 were carried out under the same conditions except that 7.3 g of L-lysine was used instead of 3.7 g of 1,3-propanediamine to yield 25.0 g of acyl group-containing composition. The analytical results are shown in Table 1.

TABLE 1

| Example | N-acyl acidic amino acid anhydride | Reactant | Reaction solvent | Reaction temp. | pH at reaction | Product purity | Dehydrate content | Free fatty acid content | Transmittance of 20% aqueous solution | N-acyl acidic amino acid content |
|---|---|---|---|---|---|---|---|---|---|---|
| Example 1 | N-lauroyl-L-glutamic acid anhydride | L-lysine hydrochloride | Water | 5° C. | 10-11 | ◎ | ◎ | ◎ | ◎ | 1~10% |
| Example 2 | N-lauroyl-D-glutamic acid anhydride | L-lysine hydrochloride | Water/tertiary butanol | 5° C. | 10-11 | ◎ | ◎ | ◎ | ◎ | 1~10% |
| Example 3 | N-lauroyl-L-glutamic acid anhydride | Octanediamine | Water | 55° C. | 11-12 | ◎ | ◎ | ◎ | ◎ | 1~10% |
| Example 4 | N-myristoyl-L-glutamic acid anhydride | L-lysine hydrochloride | Water | 15° C. | 12-13 | ◎ | ◎ | ◎ | ◎ | 1~10% |
| Example 5 | N-cocoyl-L-glutamic acid anhydride | Ethylenediamine | Water | 5° C. | 10-11 | ◎ | ◎ | ◎ | ◎ | 1~10% |
| Example 6 | N-palmitoyl-L-asparagic acid anhydride | L-lysine hydrochloride | Water/Toluene | 30° C. | 10-11 | ◎ | ◎ | ◎ | ◎ | 1~10% |
| Comparative Example 1 | N-lauroyl-L-glutamic acid anhydride | 1,3-propanediamine | Toluene | 90° C. | — | ○ | X | ◎ | X | <0.5% |
| Comparative Example 2 | N-lauroyl-L-glutamic acid anhydride | L-lysine | Toluene | 90° C. | — | ○ | X | ◎ | X | <0.5% |

EXAMPLE 7

The composition obtained in Example 1 was neutralized with sodium hydroxide to prepare an aqueous solution of solid content 30% by weight and pH 6.5. The aqueous solution was dried to produce powder of neutralized acyl group-containing composition.

EXAMPLE 8

The composition obtained in Example 5 was neutralized with sodium hydroxide to prepare an aqueous solution of solid content 30% by weight and pH 7.5. The aqueous solution was dried to produce powder of neutralized acyl group-containing composition.

EXAMPLES 9 TO 22, COMPARATIVE EXAMPLES 3 TO 6

Gelatinous compositions shown in Table 2 were produced, and the stability, utility, viscosity and transparency were evaluated for each of the compositions. The results are shown in Table 2. The composition are shown in % by weight.

(Production Process)

All of the gelatinous compositions were prepared by the following process.

The ingredients other than oil ingredients were mixed at 70° C. while stirring the mixture. Then, the oil ingredients were slowly added dropwise to the mixture while stirring. The mixture was further stirred and cooled to yield a gelatinous composition.

TABLE 2

| Ingredient (wt %) | Example 9 | Example 10 | Example 11 | Example 12 | Example 13 | Example 14 | Example 15 |
|---|---|---|---|---|---|---|---|
| Acyl-group-containing composition of Example 7 | 4 | 7.1 | | 6.8 | 1 | 1 | |
| Acyl-group-containing composition of Example 8 | | | 5 | | | | 2 |
| Sodium lauraylglutamate | 2 | | | | | | |
| Sodium lauryl diphenyl ether disulfonate | | | | | | | |
| Polyoxyethylene (5) lauryl ether | | | | | | 3 | |
| Glycerol | 30 | 28 | 21 | 24 | 31.2 | 18 | 20 |
| Diglycerol | | | | | | | |
| Sorbitol | | | | | | | |
| POE (20) methyl glycoside | | | | | | | |
| Sucrose | | | | | | | |
| Purified water | 4 | 15.9 | 4 | 9.2 | 7.8 | 10 | 13 |
| Liquid paraffin | | | | | | | |
| Isopropyl myristate | | | 70 | | | | |
| Isostearyl isostearate | | | | | | | 65 |
| Grape seed oil | | | | | | | |
| TEG + Silicone (10CS) | | | | | | | |
| Squarane | | | | | | | |
| Olive oil | 60 | 49 | | | | | |
| Silicone (10CS) | | | | | | | |
| Glyceryltri-2-ethylhexanoicacid | | | | 60 | 60 | 34 | |
| Low-boiling point silicone | | | | | | 34 | |
| Stability | ○ | ○ | ○ | ○ | ○ | ○ | ○ |
| Appearance | transparent | translucent | transparent | transparent | transparent | transparent | translucent |
| Afterfeel | ○ | ○ | ○ | ○ | ○ | ○ | ○ |
| Difference in refractive index | <0.01 | 0.05 | 0.03 | <0.01 | <0.01 | <0.01 | 0.05 |
| Viscosity (Pa·s) | >200 | 3-60 | 60-200 | 3-60 | 3-60 | 3-60 | 3-60 |
| Spreading | X | ○ | Δ | ○ | ○ | ○ | ○ |

| Ingredient (wt %) | Example 16 | Example 17 | Example 18 | Example 19 | Example 20 | Example 21 | Example 22 |
|---|---|---|---|---|---|---|---|
| Acyl-group-containing composition of Example 7 | | 6 | 1 | 5 | 1 | 5 | 6 |
| Acyl-group-containing composition of Example 8 | 3 | | | | | | |

TABLE 2-continued

| Ingredient | | | | | | | |
|---|---|---|---|---|---|---|---|
| Sodium lauraylglutamate | 3 | | | | | | |
| Sodium lauryl diphenyl ether disulfonate | | | | | | | |
| Polyoxyethylene (5) lauryl ether | | | | 2 | | | |
| Glycerol | | 32 | 14.3 | | 20 | 20 | 12 |
| Diglycerol | | | | 19 | | | |
| Sorbitol | 30 | | | | | | |
| POE (20) methyl glycoside | | | 4.8 | | | | |
| Sucrose | | | | | | | |
| Purified water | 4 | 2 | 4.6 | 4 | 2 | 0 | 22 |
| Liquid paraffin | | | | 77 | | | |
| Isopropyl myristate | | | | | | | |
| Isostearyl isostearate | | | | | | | |
| Grape seed oil | | 60 | | | | | |
| TEG + Silicone (10CS) | | | | | | | |
| Squarane | | | | 70 | | 60 | |
| Olive oil | 60 | | | | | | |
| Silicone (10CS) | | | | | | | 60 |
| Glyceryltri-2-ethylhexanoicacid | | | 75.3 | | | | |
| Low-boiling point silicone | | | | | | | |
| Stability | ○ | ○ | ○ | ○ | ○ | ○ | ○ |
| Appearance | opaque | transparent | transparent | transparent | transparent | opaque | transparent |
| Afterfeel | ○ | ○ | ○ | ○ | ○ | ○ | ○ |
| Difference in refractive index | 0.03 | <0.01 | <0.01 | <0.01 | 0.03 | >0.05 | <0.01 |
| Viscosity (Pa·s) | >200 | >200 | 3-60 | >200 | >200 | >200 | <1 |
| Spreading | X | X | ○ | X | X | X | Δ |

| Ingredient (wt %) | Comparative Example 3 | Comparative Example 4 | Comparative Example 5 | Comparative Example 6 |
|---|---|---|---|---|
| Acyl-group-containing composition of Example 7 | | | | |
| Acyl-group-containing composition of Example 8 | | | | |
| Sodium lauraylglutamate | 11 | 4 | | |
| Sodium lauryl diphenyl ether disulfonate | | | 13 | |
| Polyoxyethylene (5) lauryl ether | | | | 12 |
| Glycerol | 17 | 17 | 17 | 20 |
| Diglycerol | | | | |
| Sorbitol | | | | |
| POE (20) methyl glycoside | | | | |
| Sucrose | | | | |
| Purified water | 14 | 10 | 12 | 5 |
| Liquid paraffin | | | | |
| Isopropyl myristate | | | | |
| Isostearyl isostearate | | | | |
| Grape seed oil | | | | |
| TEG + Silicone (10CS) | | | | |
| Squarane | | 69 | | |
| Olive oil | 58 | | 58 | 63 |
| Silicone (10CS) | | | | |
| Glyceryltri-2-ethylhexanoicacid | | | | |
| Low-boiling point silicone | | | | |
| Stability | X | X | X | X |
| Appearance | separated | separated | separated | separated |
| Afterfeel | X | X | X | X |
| Difference in refractive index | — | — | — | — |
| Viscosity (Pa·s) | — | — | — | — |
| Spreading | — | — | — | — |

EXAMPLES 23-24

The gelatinous composition produced in Example 21 was stirred at 70° C., the oil phase portion was added to the composition while stirring at 70° C., the remaining water phase portion was added to 100 parts by weight in all, and the mixture was cooled to produce a formulation. The stability and afterfeel were evaluated. The results are shown in Table 3. The compositions in Table 3 are shown in terms of % by weight.

COMPARATIVE EXAMPLE 7

The oil phase portion and the water phase portion shown in Comparative Example 7 in Table 3 were respectively heated to 70° C. and dissolved, then the oil phase portion was mixed and emulsified with the water phase portion, and the mixture was cooled to yield a formulation. The stability and afterfeel were evaluated for the formulation. The results are shown in Table 3. The formulation composition in Table 3 is shown in terms of % by weight.

TABLE 3

|  | Example 23 Lotion | Example 24 Cream |
|---|---|---|
| (Oil gel) |  |  |
| Squarane | 13 | 13 |
| Composition of Example 7 | 1 | 1 |
| Glycerol | 6 | 6 |
| (Oil phase) |  |  |
| Stearic acid | 2 | 3 |
| Cetanol | 1.5 | 5 |
| Vaseline |  | 5 |
| Glyceryl tri-2-ethylhexanoate |  | 4 |
| (Water phase) |  |  |
| Triethanolamine | 0.5 | 1 |
| Citric acid | Suitable amount | Suitable amount |
| Purified water | rest | rest |
| Stability | ○ | ○ |
| Afterfeel | ○ | ○ |

|  | Comparative Example 7 Cream |
|---|---|
| (Oil phase) |  |
| Squarane | 13 |
| Stearic acid | 2 |
| Cetanol | 1.5 |
| Vaseline | 5 |
| Glyceryl tri-2-ethylhexanoate | 4 |
| (Water phase) |  |
| Triethanolamine | 0.5 |
| Citric acid | Suitable amount |
| Composition of Production Example 1 | 0.05 |
| Glycerol | 6 |
| Purified water | rest |
| Stability | X |
| Afterfeel | X |

REFERENCE EXAMPLE 1

The moisture absorption rate under high humidity and the moisture retention rate under low humidity were evaluated for the composition produced in Example 7 and urea as a contrast. Specifically, 1 g of dried sample was dried in a weighing bottle and weighed precisely, and left stand in a desiccator under relative humidity as high as 84% at 25° C. while measuring the sample weight with time until 313 hours has elapsed. Then, the same sample was transferred into a desiccator under relative humidity as low as 33% at 25° C., and left stand in the desiccator while measuring the sample weight with time in the same manner as above considering the point 313 hours has elapsed as a test starting point (0 hr). The moisture absorption rate was obtained in accordance with the following equation. Moisture absorption rate (%)=(Wt−W0/W0)×100 W0: dry weight before being left stand, Wt: weight at the time of each measuring The results are shown in Table 4. Urea showed its deliquescent properties during the course of moisture absorption, but once it was left stand under low humidity, it released almost all its moisture. On the other hand, the acyl group-containing composition produced in Example 7 did not have deliquescent properties and showed high moisture retention compared with urea.

TABLE 4

| | Moisture absorption rates under high humidity after different elapsed time (%) | | | | | |
|---|---|---|---|---|---|---|
| Sample | 5 Hr | 27 Hr | 48 Hr | 120 Hr | 197 Hr | 313 Hr |
| Composition of Example 7 | 7.9 | 26.8 | 35.0 | 43.1 | 44.2 | 44.7 |
| Urea | 0.2 | 3.2 | 7.4 | 24.7 | 42.6 | 72.7 |

| | Moisture absorption rates under low humidity after different elapsed time (%) | | | | |
|---|---|---|---|---|---|
| Sample | 0 Hr | 25 Hr | 49 Hr | 75 Hr | 141 Hr |
| Composition of Example 7 | 44.7 | 22.3 | 10.9 | 7.8 | 7.0 |
| Urea | 72.7 | 1.2 | 0.3 | 0.4 | 0.3 |

EXAMPLES 25 TO 26, COMPARATIVE EXAMPLE 8

A skin lotion was prepared using the acyl group-containing composition produced in Example 7 so that it has a composition shown in Table 5 and evaluation was conducted for the skin lotion. The results are shown in Table 5. The composition in Table 5 is shown in terms of % by weight.

The skin lotion prepared using the acyl group-containing composition produced in Example 7 had an excellent afterfeel.

TABLE 5

|  | Example 25 | Example 26 | Comparative Example 8 |
|---|---|---|---|
| Composition of Example 7 | 0.5 | 1 | 0 |
| Urea | 0 | 0 | 1 |
| 1,3-Butylene glycol | 5 | 2 | 2 |
| Oleyl alchol | 0.1 | 0 | 0 |
| Ethanol | 5 | 10 | 10 |
| Purified water | rest | rest | rest |
| pH | 6.5 | 6.5 | 6.5 |
| afterfeel | ○ | ○ | X |

EXAMPLE 27

The composition produced in Example 7 was used as a dispersant. The dispersant was added to 300 ml of purified water so that the solid content concentration was 0.01% by weight, fine-grained titanium oxide (ISHIHARA SANGYO KAISHA, LTD.; "TTO-55(A)", trademark) as a pigment was added to the above solution so that the solid content concentration was 1% by weight, and the mixed solution was stirred and dispersed for 2 minutes with a homomixer at 10000 rpm and normal temperature. The dispersion was left stand at 40° C. and the transmittance of the supernatant at 300 nm was measured with time. The results are shown in Table 6.

Since the fine-grained titanium oxide exerts its ultraviolet ray screening effect when being dispersed, smaller transmittance measurements indicate that the titanium oxide is neither aggregated nor precipitated, but stably dispersed. From this point of view, the composition of Example 27 has excellent dispersion stability.

COMPARATIVE EXAMPLES 9 TO 11

The transmittance of the supernatant at 300 nm was measured with time in the same manner as Example 27 except that the dispersant used in Example 27 was replaced by the following ones. The results are shown in Table 6.

Comparative Example 9; sodium lauroylglutamate
Comparative Example 10; polyethyleneglycol(20) monostearate
Comparative Example 11; polyoxyethylene(20) sorbitan-monolaurate

TABLE 6

| | | Change in transmittance of supernatant with time (T %) | | | | | | |
|---|---|---|---|---|---|---|---|---|
| | Dispersant | 0 Hr | 5 Hr | 30 Hr | 50 Hr | 75 Hr | 100 Hr | 200 Hr |
| Example 27 | Composition of Example 7 | 1.4 | 1.3 | 1.2 | 1.3 | 1.2 | 0.9 | 0.8 |
| Comparative Example 9 | Sodium lauroylglutamate | 1.4 | 83.2 | 98.6 | 100 | 100 | 100 | 100 |
| Comparative Example 10 | Polyethylene glycol(20) monostearate | 1.4 | 1.3 | 1.2 | 13.5 | 81.3 | 85.1 | 97.3 |
| Comparative Example 11 | Polyoxyethylene(20) sorbitan monolaurate | 1.4 | 1.7 | 3.2 | 10.0 | 9.9 | 84.5 | 88.5 |

EXAMPLE 28, COMPARATIVE EXAMPLES 12 TO 13

The transmittance of the supernatant was measured with time under the same conditions as Example 27 except that activated carbon (Takeda Chemical Industries, Ltd., trademark: "Shirasagi") was used as a pigment instead of fine-grained titanium oxide, the dispersant used in Example 27 was replaced by the following ones and the transmittance was measured at 300 nm and at 660 nm. The results are shown in Table 7. Smaller transmittance measurements indicate that the activated carbon is neither aggregated nor precipitated, but stably dispersed. From this point of view, the composition of Example 7 has particularly excellent dispersion stability.

Example 28; composition of Example 7
Comparative Example 12; sodium lauroylglutamate
Comparative Example 13; polyethyleneglycol(20) monostearate
Comparative Example 14; polyoxyethylene(20) sorbitan-monolaurate

TABLE 7

| | | Change in transmittance of supernatant with time (T %) | | | | |
|---|---|---|---|---|---|---|
| | Dispersant | 0 Hr | 5 Hr | 30 Hr | 80 Hr | 150 Hr |
| Example 28 | Composition of Example 7 | 0.6 | 0.6 | 0.6 | 0.7 | 0.8 |
| Comparative Example 12 | Sodium lauroylglutamate | 0.6 | 0.6 | 0.6 | 0.7 | 5.7 |
| Comparative Example 13 | Polyethylene glycol(20) monostearate | 0.6 | 0.6 | 2.8 | 3.6 | 24.7 |
| Comparative Example 14 | Polyoxyethylene (20) sorbitan monolaurate | 0.6 | 0.6 | 1.1 | 4.4 | 23.0 |

INDUSTRIAL APPLICABILITY

The acyl group-containing composition of this invention is an anionic surfactant which is applicable to the field of cosmetics such as cleansing agents, quasi drugs and makeups. It is a surfactant which shows surface activity at low concentrations, is less irritating to the skin and has moisture retention. The acyl group-containing composition is applicable to: cosmetics that do not leave the skin feeling sticky, but provide a moist feeling to improve the skin moisturizing effect; gelatinous compositions that can have arbitrary hardness from the hardness of a paste to that of a solid; cleansing agents that have an excellent afterfeel; and dispersants for pigments that have excellent dispersibility.

What is claimed is:

1. A method of producing an acyl group-containing composition containing at least one acyl compound represented by the general formula (2) comprising a step of reacting a long chain N-acyl acidic amino acid anhydride represented by the following formula (1):

[Formula 1]

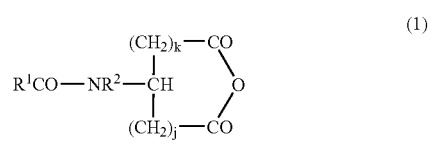

wherein R¹CO represents a long chain acyl group derived from a saturated or unsaturated fatty acid with 2 to 20 carbon atoms; R² is hydrogen or a lower alkyl group with 1 to 3 carbon atoms which is optionally substituted with a hydroxyl or carboxyl group; j, k are independently any of 0, 1 and 2 and are not 0 at the same time, with one or more compounds having, per molecule, m functional groups of one kind or more selected from the group consisting of hydroxyl, amino and thiol groups in an aqueous solvent and/or a mixed solvent of water and an organic solvent, wherein the acyl group-containing composition comprises at least one acyl compound represented by the following general formula (2):

[Formula 2]

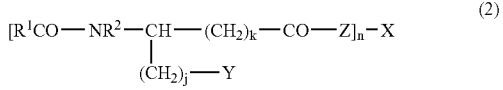

(2)

wherein R¹CO, R², and j, k each represent the same as those defined in the above formula (1); n (n is an integer of 2 to 20, including 2 and 20) Zs are bonding portions to which m (m≧n) functional groups of one kind or more selected from the group consisting of hydroxyl, amino and thiol groups substituted on X bind and which are selected independently from the group consisting of —O—, —NR³— (R³ is hydrogen, or an alkyl, an alkenyl, an aryl or an alkylaryl group with 1 to 10 carbon atoms) and —S—; X is a spacer of a straight, branched or cyclic hydrocarbon chain of molecular weight of 1,000,000 or less which optionally has substituents other than hydroxyl, amino and thiol groups and contains or does not contain an aromatic hydrocarbon; n substituents represented by the following general formula (3):

[Formula 3]

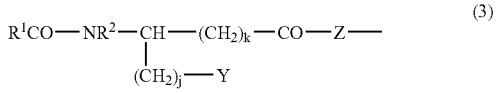

(3)

wherein reference characters each represent the same as those defined in the above formula (2), which are attached to X via Z are independent of each other; and Y represents a carboxyl group or the salt thereof.

2. The method according to claim 1, wherein in the general formula (2), X is a spacer of a straight, branched or cyclic hydrocarbon chain with 1 to 40 carbon atoms which optionally has substituents other than hydroxyl, amino and thiol groups and contains or does not contain an aromatic hydrocarbon.

3. The method according to claim 1 or 2, wherein in said reaction step, the molar ratio of the total of the functional groups contained in the one or more compounds having, per molecule, m functional groups of one kind or more selected from the group consisting of hydroxyl, amino and thiol groups to the long chain N-acyl acidic amino acid anhydride represented by the formula (1) is 0.5 to 1.4 and the pH of the reaction solution is kept at 4 to 14 at the time of reaction.

4. The method according to claim 1 or 2, further comprising, as step(s) carried out after said reaction step, either one or both of (i) a step of separating the reaction solution derived from said reaction step into two layers, an organic layer and a water layer, by adjusting the pH of the reaction solution to 1 to 6 using a mineral acid to obtain an organic layer which contains the acyl group-containing composition, which is defined as an acid-precipitation and layer-separation step and (ii) a step of separating, at 35° C. to 80° C., the mixture of the acyl group-containing composition, which contains water-soluble impurities such as inorganic salts, and the medium, which substantially contains water and tertiary butanol as main ingredients, into a water layer and an organic layer containing the acyl group-containing composition to remove impurities in the acyl group-containing composition, which is defined as a washing step.

5. The method according to claim 1 or 2, wherein after said reaction step, or after said acid-precipitation and layer-separation step or washing step, the organic solvent is distilled off from the organic layer, which contains the acyl group-containing composition, using a spray evaporator in which a mixed solution is allowed to take the form of a vapor-liquid mixed phase and is sprayed within the evaporator to evaporate the solvent.

* * * * *

UNITED STATES PATENT AND TRADEMARK OFFICE
CERTIFICATE OF CORRECTION

| | | Page 1 of 1 |
|---|---|---|
| PATENT NO. | : 7,488,841 B2 | |
| APPLICATION NO. | : 10/525729 | |
| DATED | : February 10, 2009 | |
| INVENTOR(S) | : Yamawaki et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 910 days.

Signed and Sealed this
Seventeenth Day of May, 2011

David J. Kappos
*Director of the United States Patent and Trademark Office*